United States Patent
Rubenstein et al.

(10) Patent No.: US 6,689,085 B1
(45) Date of Patent: *Feb. 10, 2004

(54) METHOD AND APPARATUS FOR TREATING ADULT-ONSET DEMENTIA OF THE ALZHEIMER'S TYPE

(75) Inventors: Edward Rubenstein, Hillsborough, CA (US); David L. Karshmer, Menlo Park, CA (US); Elliott C. Levinthal, Atherton, CA (US); Jaime S. Vargas, Stanford, CA (US); Tom A. Saul, El Granada, CA (US)

(73) Assignee: Eunoe, Inc., Redwood City, CA (US)

(*) Notice: Subject to any disclaimer, the term of this patent is extended or adjusted under 35 U.S.C. 154(b) by 366 days.

This patent is subject to a terminal disclaimer.

(21) Appl. No.: 09/654,967

(22) Filed: Sep. 5, 2000

Related U.S. Application Data

(60) Division of application No. 08/901,023, filed on Jul. 25, 1997, now Pat. No. 6,264,625, which is a continuation-in-part of application No. 08/678,191, filed on Jul. 11, 1996, now Pat. No. 5,980,480.

(51) Int. Cl.[7] ............................................... A61M 5/00
(52) U.S. Cl. ............................................. 604/9; 604/8
(58) Field of Search ........................................ 604/8–10

(56) References Cited

U.S. PATENT DOCUMENTS

| | | | |
|---|---|---|---|
| 3,654,932 A | * | 4/1972 | Newkirk et al. ............... 604/9 |
| 3,864,259 A | * | 2/1975 | Newhart ................... 604/6.06 |
| 3,886,948 A | | 6/1975 | Hakim |
| 4,156,422 A | | 5/1979 | Hildebrandt et al. |
| 4,261,341 A | | 4/1981 | Hakim et al. |
| 4,375,816 A | | 3/1983 | Labianca |
| 4,560,375 A | | 12/1985 | Schulte et al. |
| 4,598,579 A | | 7/1986 | Cummings et al. |

(List continued on next page.)

FOREIGN PATENT DOCUMENTS

| | | |
|---|---|---|
| EP | 115973 | 8/1984 |
| EP | 117695 | 9/1984 |
| EP | 478842 | 4/1992 |
| FR | 2354103 | 1/1978 |
| FR | 2685206 | 6/1993 |

OTHER PUBLICATIONS

Adams et al., "Disturbances of cerebrospinal fluid circulation, including hydrocephalus and meningeal reactions," *Principles of Neurology*, Fourth Edition, Chapter 30, 1989, pp. 501–502.

Adams, R.D. et al., "Symptomatic occult hydrocephalus with 'normal' cerebrospinal–fluid pressure" *The New England Journal of Medicine*, vol. 273, No. 3, pp. 117–126 (Jul. 15, 1965).

Appenzeller, Otto & Salmon, James H., Treatment of parenchymatous degeneration of the brain by ventriculo–atrial shunting of the cerebrospinal fluid, *Journal of Neurosurgery*, vol. XXVI, pp. 478–482, (Jan.–Jun. 1967).

Arai et al., "Tau cerebrospinal fluid: a potential diagnostic marker," *Ann. Neurology*, vol. 38, 1995, pp. 649–652.

(List continued on next page.)

*Primary Examiner*—Brian L. Casler
*Assistant Examiner*—Jeremy Thissell
(74) *Attorney, Agent, or Firm*—Townsend and Townsend and Crew LLP

(57) ABSTRACT

A method for treating a patient for adult-onset dementia of the Alzheimer's type by removing a portion of the patient's cerebrospinal fluid, preferably (although not necessarily) by transporting the fluid to another portion of the patient's body. The invention also provides an apparatus for removing cerebrospinal fluid including (1) a conduit with a first opening and a second opening, the first opening of the conduit being adapted to be disposed in fluid communication with a space within a patient's subarachnoid space, the second opening being adapted to be disposed in fluid communication with another portion of the patient's body; and (2) a flow rate control device attached to the conduit.

12 Claims, 19 Drawing Sheets

U.S. PATENT DOCUMENTS

| | | | |
|---|---|---|---|
| 4,605,395 A | 8/1986 | Rose et al. | |
| 4,610,658 A | 9/1986 | Buchwald et al. | |
| 4,673,384 A | 6/1987 | Marion | |
| 4,675,003 A | 6/1987 | Hooven | |
| 4,681,559 A | 7/1987 | Hooven | |
| 4,713,065 A | * 12/1987 | Koot | 604/329 |
| 4,933,156 A | 6/1990 | Quay et al. | |
| 4,950,232 A | 8/1990 | Ruzicka et al. | |
| 5,039,511 A | 8/1991 | Quay | |
| 5,069,663 A | 12/1991 | Sussman | |
| 5,167,615 A | 12/1992 | East et al. | |
| 5,334,315 A | 8/1994 | Matkovich et al. | |
| 5,336,166 A | 8/1994 | Sierra | |
| 5,368,556 A | 11/1994 | Lecuyer | |
| 5,385,541 A | 1/1995 | Kirsch et al. | |
| 5,387,188 A | 2/1995 | Watson | |
| 5,425,368 A | 6/1995 | Brandt | |
| 5,462,667 A | 10/1995 | Wollinsky et al. | |
| 5,601,985 A | 2/1997 | Trojanowski et al. | |
| 5,643,194 A | 7/1997 | Negre | |
| 5,643,195 A | 7/1997 | Drevet et al. | |
| 5,980,480 A | 11/1999 | Rubenstein et al. | |

OTHER PUBLICATIONS

Bannister, Roger, et al., "Isotope encephalography in the diagnosis of dementia due to communicating hydrocephalus" *The Lancet*, pp. 1014–1017, (Nov. 11, 1967).

Barnett et al., "Normal pressure hydrocephalus in children and young adults" *Neurosurgery* (1987) 20(6):904–907.

Boon et al., "Does CSF outflow resistance predict the response to shunting in patients with normal pressure hydrocephalus?" *Acta Neurochir.* (1998) 71:331–333.

Boon et al., "Dutch normal–pressure hydrocephalus study: Prediction of outcome after shunting by resistance to outflow of cerebrospinal fluid" *J. Neurosurg.* (1997) 87:687–693.

Bush et al., "Beta A–4 amyloid protein and its precursor in Alzheimer's disease," *Pharmac. Tera.*, vol. 56, 1992, pp. 97–117.

Chen, I.H. et al., "Effectiveness of shunting in patients with normal pressure hydrocephalus predicted by temporary, controlled–resistance, continuous lumbar drainage: a pilot study," *Journal of Neurology, Neurosurgery, and Psychiatry*, 1994, S/1430–1432.

Clarfield, "Normal–pressure hydrocephalus: Saga or swamp?" *JAMA* (1989) 262(18):2592–2593.

Damasceno et al., "The predictive value of cerebrospinal fluid tap–test in normal pressure hydrocephalus" *Arq. Neurosiquiatr.* (1997) 55(2):179–185.

Friedland, "Normal–pressure hydrocephalus and the saga of the treatable dementias" *JAMA* (1989) 262(18):2577–2581.

Golomb et al., "Alzheimer's disease comorbidity in normal pressure hydrocephalus: prevalence and shunt response" *J. Neurol. Neurosurg. Psych.* (2000) 68:778–781.

Graff–Radford et al., "Normal–pressure hydrocephalus" *Neurol.* (1986) 43:940–942.

Gustafson et al., "Recovery in hydrocephalic dementia after shunt operation" *J. Neurol. Neurosurg. Psych.* (1978) 41:940–947.

Hakim et al., "The special clinical problem of symptomatic hydrocephalus with normal cerebrospinal fluid pressure. Observations on cerebrospinal fluid hydrodynamics" *J. Neurol. Sci.* (1965) 2:307–327.

Holodny et al. "Focal dilation and paradoxical collapse of cortical fissures and sulci in patients with normal–pressure hydrocephalus" J. Neurosurg. (1998) 89:742–747.

Kaye et al., "Plasticity in the aging brain" *Arch Neurol.* (1990) 47:1336–1341.

Ko et al., "Cerebrospinal fluid control system" Proceedings of the IEEE, vol. 76, No. 9, pp. 1226–1235, Sep. 1988.

Martinez et al., "Relationship of interleukin–1 beta and beta$_2$–microglobulin with neuropeptides in cerebrospinal fluid of patients with dementia of the Alzheimer type," *J. Neuroimmunology*, vol. 48, 1993, pp 235–240.

Mataró et al., "Cognitive changes after cerebrospinal fluid shunting in young adults with spina bifida and assumed arrested hydrocephalus" *J. Neurol. Neurosurg. Psych.* (2000) 68:615–621.

Mogilner et al., "Hydrocephalus: Does coexistent Alzheimer's disease affect outcome?" *Poster Presentation from AANS 1999* New Orleans, http://cnshome.org/abstrats, 2 pages total.

Nakamura et al., "Amyloid beta protein levels in cerebrospinal fluid are elevated in early–onset Alzheimer's disease," *Ann. Neurology*, vol. 36, 1994, pp. 903–911.

Ono et al., "Formation of amyloid–like substance from beta–2 microglobulin in vitro. Role of serum amyloid P component: a preliminary study," *Nephron.* vol. 66, 1994, pp. 404–407.

Salmon, James H., "Senile and presenile dementia" *Geriatrics* (Dec. 1969) 24 (12) : 67–72.

Shenkin et al., "Ventricular shunting for relief of senile symptoms" *JAMA* (1973) 225(12):1486–1489.

SkinhØj, Erik, "Determination of regional cerebral blood-flow in man" Head injury conference , held at the University of Chicago Center for Continuing Education with Joseph P. Evans as host. No. 34, pp. 431–438.

Vanneste et al., "Shunting normal–pressure hyrocephalus: Do the benefits outweigh the risks?" *Neurol.* (1992) 42:54–59.

Vorstrup et al., "Cerebral blod flow in patients with normal–pressure hydrocephalus before and after shunting" *J. Neurol.* (1987) 66:379–387.

Williams et al., "Evaluation of shunt function in patients who are never better, or better than worse after shunt surgery for NPH" *Acta Neurochir.* (1998) 71:368–370.

Williams et al., "Comparison of Pcsf monitoring and controlled CSF drainage diagnose normal pressure hydrocephalus" *Acta Neurochir.* (1998) 71:328–330.

Committee on Medical Rating of Physical Impairment (McKeown, Raymond M. et al.,) The Central Nervous System, *JAMA*, "The Journal" Fifth in a series pp. 24–35, (Jul. 6, 1963).

\* cited by examiner

METHOD AND APPARATUS FOR TREATING ADULT-ONSET DEMENTIA OF THE ALZHEIMER'S TYPE

This application is a division of and claims the benefit of U.S. application Ser. No. 08/901,023, filed Jul. 25, 1997, now U.S. Pat. No. 6,264,625 which is a continuation-in-part of application Ser. No. 08/678,191, filed Jul. 11, 1996, now U.S. Pat. No. 5,980,480 the entire disclosures of which are hereby incorporated by reference.

BACKGROUND OF THE INVENTION

This invention relates generally to a method and apparatus for treating patients with adult-onset dementia. In particular, the invention relates to a method and apparatus for increasing the clearance of substances from the cerebrospinal fluid in certain patients with adult-onset dementia of the Alzheimer's type.

The brain and spinal cord are encased within the cranium and vertebral column inside a thin membrane known as the arachnoid. The volume of the intracranial space is on average about 1700 ml. The volume of the brain is approximately 1400 ml, the volume of the intracranial blood is approximately 150 ml; the remaining 150 ml is filled with cerebrospinal fluid. The cerebrospinal fluid circulates within the subarachnoid space. It is formed principally by the choroid plexuses, which secrete about 80% of the total volume. The sources of the remainder are the vasculature of the subependymal regions, and the pia mater. The total volume of the cerebrospinal fluid is renewed several times per day, so that about 500 ml are produced every 24 hours.

The cerebrospinal fluid is absorbed through the arachnoid villi, located principally over the superior surfaces of the cerebral hemispheres. Some villi also exist at the base of the brain and along the roots of the spinal nerves. The absorptive processes include bulk transport of large molecules and as well as diffusion across porous membranes of small molecules. (Adams et al. (1989) "principles of Neurology," pp. 501–502).

The principle on which this invention is based is that in some persons with adult-onset dementia of the Alzheimer's type there is dysfunction of the cerebrospinal fluid resorptive mechanism, leading to the retention in the cerebrospinal fluid of substances which result in the histologic lesions associated with adult-onset dementia of the Alzheimer's type, or which are neurotoxic, or both.

There are several examples of low-molecular weight proteins or peptides that are known to be present in elevated concentrations in the cerebrospinal fluid of persons suffering from adult-onset dementia of the Alzheimer's type. For example, elevated levels of beta A-4 amyloid have been found in the cerebrospinal fluid of patients with early-onset Alzheimer's disease. (Nakamura et al., (1994) "Amyloid beta protein levels in cerebrospinal fluid are elevated in early-onset Alzheimer's disease," *Ann. Neurology* 36:903–911). Beta A-4 amyloid is known to self-aggregate into molecules of amyloid of the type that typify the core plaques found in the brain in persons suffering from adult-onset dementia of the Alzheimer's type. In fact, beta A-4 amyloid deposition in the brain is the only microscopic lesion specific for Alzheimer's disease. Furthermore, beta A-4 amyloid has been shown to be neurotoxic. (Bush et al., (1992) "Beta A-4 amyloid protein and its precursor in Alzheimer's disease," *Pharmac. Tera.* 56:97–117). Beta A-4 amyloid is also a component of microscopic cerebral lesions known as neurofibrillary tangles, characteristically found in adult-onset dementia of the Alzheimer's type.

Beta-2 microglobulin is another example of a low-molecular-weight protein whose concentration in the cerebrospinal fluid increases with age and reaches high levels in patients with adult-onset dementia of the Alzheimer's type. (Martinez et al., (1993) "Relationship of interleukin-1 beta and beta$_2$-microglobulin with neuropeptides in cerebrospinal fluid of patients with dementia of the Alzheimer type," *J. Neuroimmunology* 48:235–240). Beta-2 microglobulin is associated with amyloid deposits in some tissues of patients on long-term renal hemodialysis. (Ono et al., (1994) "Formation of amyloid-like substance from beta-2-microglobulin in vitro. Role of serum amyloid P component: a preliminary study," *Nephron* 66:404–407).

Another substance that accumulates in the cerebrospinal fluid in patients with adult-onset dementia of the Alzheimer's type is tau, a component of the neurofibrillary tangles found in involved brain tissue. Tau concentrations in cerebrospinal fluid are regularly increased in this syndrome with eight fold increases present in half of the patients. (Arai et al., (1995) "Tau in cerebrospinal fluid: a potential diagnostic marker," *Ann. Neurology* 38:649–652).

In addition, the prior art also describes devices used to remove cerebrospinal fluid from a patient. Matkovich U.S. Pat. No. 5,334,315 describes a method and device that can be used to remove a body fluid from a patient, to treat that fluid to remove an undesirable component, and to return the fluid to the patient. Matkovich's partial list of the kinds of deleterious or undesirable substances that can be removed from a fluid includes proteins, polypeptides, interleukins, immunoglobulins, proteases and interferon. The fluids from which these substances can be removed using the Matkovich apparatus include cerebrospinal fluid, blood, urine and saliva. Matkovich never suggests, however, that his method and apparatus could be used to treat patients suffering from adult-onset dementia of the Alzheimer's type.

Kirsch et al. U.S. Pat. No. 5,385,541 describes a cerebrospinal fluid shunt mechanism used to treat hydrocephalus by draining cerebrospinal fluid into the patient's abdomen, chest or vascular system. The system may include a one-way valve to prevent backflow. Kirsch et al. does not describe the use of such a system to treat adult-onset dementia of the Alzheimer's type, however.

Ruzicka et al. U.S. Pat. No. 4,950,232 discloses another cerebrospinal fluid shunt system. As with the Kirsch et al. patent, Ruzicka does not suggest the use of his shunt system to treat adult-onset dementia of the Alzheimer's type.

Chen et al. (1994) "Effectiveness of Shunting in patients with normal pressure hydrocephalus predicted by temporary, controlled-resistance, continuous lumbar drainage: a pilot study," *J. Neurol. Neurosurg. Psychiatry* 51:1430–1432, describes use of a "silicon" catheter for draining CSF from the subarachnoid region into an external collection bag.

DISCLOSURE OF THE INVENTION

Although the prior art has recognized the presence of elevated concentrations of certain substances in the cerebrospinal fluid of persons suffering from adult-onset dementia of the Alzheimer's type, the prior art has not provided a method of correcting this imbalance. One objective of this invention, therefore, is to provide such a treatment. Thus, in a preferred embodiment, the invention is a method for treating a patient for adult-onset dementia of the Alzheimer's type by removing a portion of the patient's cerebrospinal fluid, preferably (although not necessarily) by transporting the fluid to another portion of the patient's body.

In addition, although the prior art has provided shunt devices to remove excess cerebrospinal fluid from patients suffering from hydrocephalus, the prior art has not recognized the use of these devices to treat adult-onset dementia of the Alzheimer's type by removing cerebrospinal fluid that is not excessive in volume. Another objective of this invention is to provide an apparatus designed to transport cerebrospinal fluid at a controlled rate. The invention therefore also provides an apparatus for removing cerebrospinal fluid including (1) a conduit with a first opening and a second opening, the first opening of the conduit being adapted to be disposed in fluid communication with a space within a patient's subarachnoid space, the second opening being adapted to be disposed in fluid communication with another portion of the patient's body; and (2) a flow rate control device attached to the conduit.

The present invention provides methods, systems, apparatus, and kits for removing cerebrospinal fluid from a patient in a controlled manner, particularly for the treatment of Alzheimer's disease. The cerebrospinal fluid is preferably removed at a rate sufficient to reduce or eliminate, preferably eliminate the progression of Alzheimer's disease in patients. Usually, the removal rate will be in the range from 5% to 50% of the patient replacement rate (typically in the range from 250 ml/day to 300 ml/day), more usually from 10% to 20% of the replacement rate. At present, the preferred removal rate is in the range from 0.5 ml/hour to 15 ml/hour, preferably from 1 ml/hour to 5 ml/hour, more preferably from 1 ml/hour to 3 ml/hour, based on the average removal rate over a 24-hour period. It will be appreciated, however, that the particular removal rate which is effective with any individual patient may vary from within the preferred ranges set forth above, and any removal rate which results in significant lowering of the concentration of the factors associated with Alzheimer's disease may have a therapeutic effect.

The invention will be described in more detail below with reference to the drawings.

DESCRIPTION OF THE SPECIFIC EMBODIMENT

In its most general terms, the method and apparatus of this invention treat a patient suffering from adult-onset dementia of the Alzheimer's type by removing a portion of the patient's cerebrospihal fluid. Since the patient is able to replace the removed fluid, removal of the cerebrospinal fluid has the effect of diluting the concentration of any deleterious materials in the patient's cerebrospinal fluid, such as neurotoxic substances and substances associated with histologic lesions. However, since removal of cerebrospinal fluid at too great a rate could be harmful to the patient, the invention preferably controls the rate of transport of cerebrospinal fluid.

Figure 1:
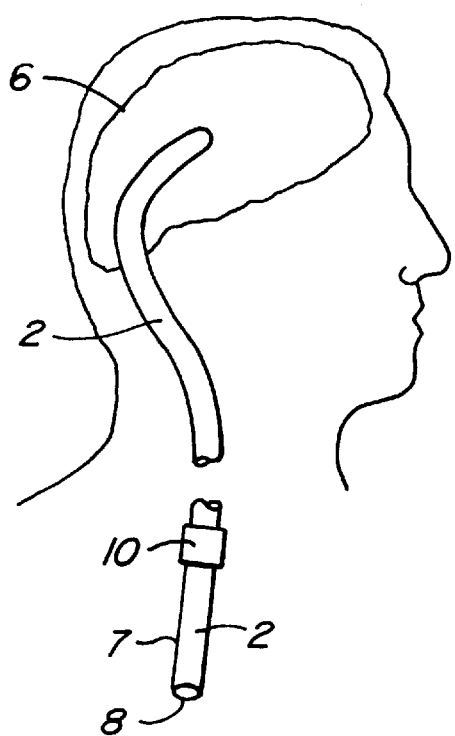
FIG. 1 illustrates an apparatus constructed according to the principles of the present invention showing its use in a patient.

As diagrammatically shown in FIG. 1, the preferred apparatus of this invention includes a conduit or catheter 2 having a first or inlet end portion positioned in a space within the patient's subarachnoid space 6, preferably in one of the lateral ventricles. The ventricles form a group of interconnected cavities that are located within the cerebral hemispheres and brain stem. These ventricles or spaces are continuous with the central canal of the spinal cord and are similarly filled with cerebrospinal fluid.

The conduit or catheter 2 may comprise two or more distinct segments or portions, each of which is a separate tube, connector, module, or the like, as described in more detail below. The inlet portion of the catheter 2 may be in any form which is suitable for placement within the subarachnoid space 6 and which is capable of collecting cerebrospinal fluid from the region of the subarachnoid space. Conveniently, the form of the inlet end of catheter 2 may be similar or identical to conventional ventricular catheters of the type used for draining cerebrospinal fluid for treating hydrocephalus, such as those described in U.S. Pat. Nos. 5,385,541 and 4,950,232, the full disclosures of which are incorporated herein by reference. Suitable ventricular catheters which can be incorporated into catheter systems according to the present invention are available from commercial suppliers, such as Medtronic PS Medical, Goleta, Calif.

Figure 7:
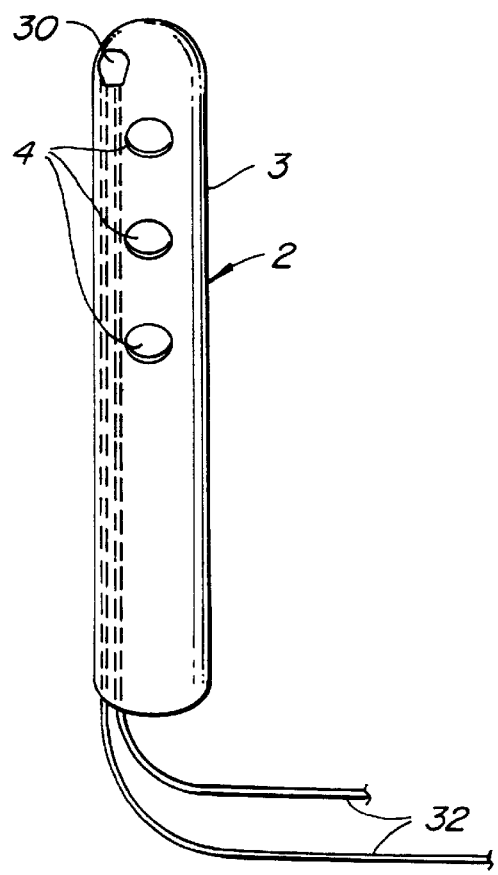
FIG. 7 shows a pressure transducer for sensing cerebrospinal fluid pressure and controlling the flow rate of cerebrospinal fluid.

One inlet end portion construction is shown, for example, in FIG. 7 and designated with reference numeral 3. As noted above, inlet end portion 3 preferably is adapted for placement in one of the ventricles for removing cerebrospinal fluid therefrom. The end portion preferably includes multiple perforations or holes 4 spaced from the tip of portion 3. These holes preferably do not extend more than about 1 to 1.5 cm from the tip. Although a particular inlet hole arrangement is shown, arrangements can be used without departing from the scope of the invention. Conduit 2 preferably comprises biocompatible material suitable for implantation in the patient such as implant grade low bending modulus material that is generally kink resistant. Conduit 2 may, for example, comprise silicone or reinforced silicone, or medical shunt tubing may be used. The tubing may have an outer diameter of about 2.0 mm and an inner diameter of about 0.5–1.5 mm.

Figures 11, 13A:
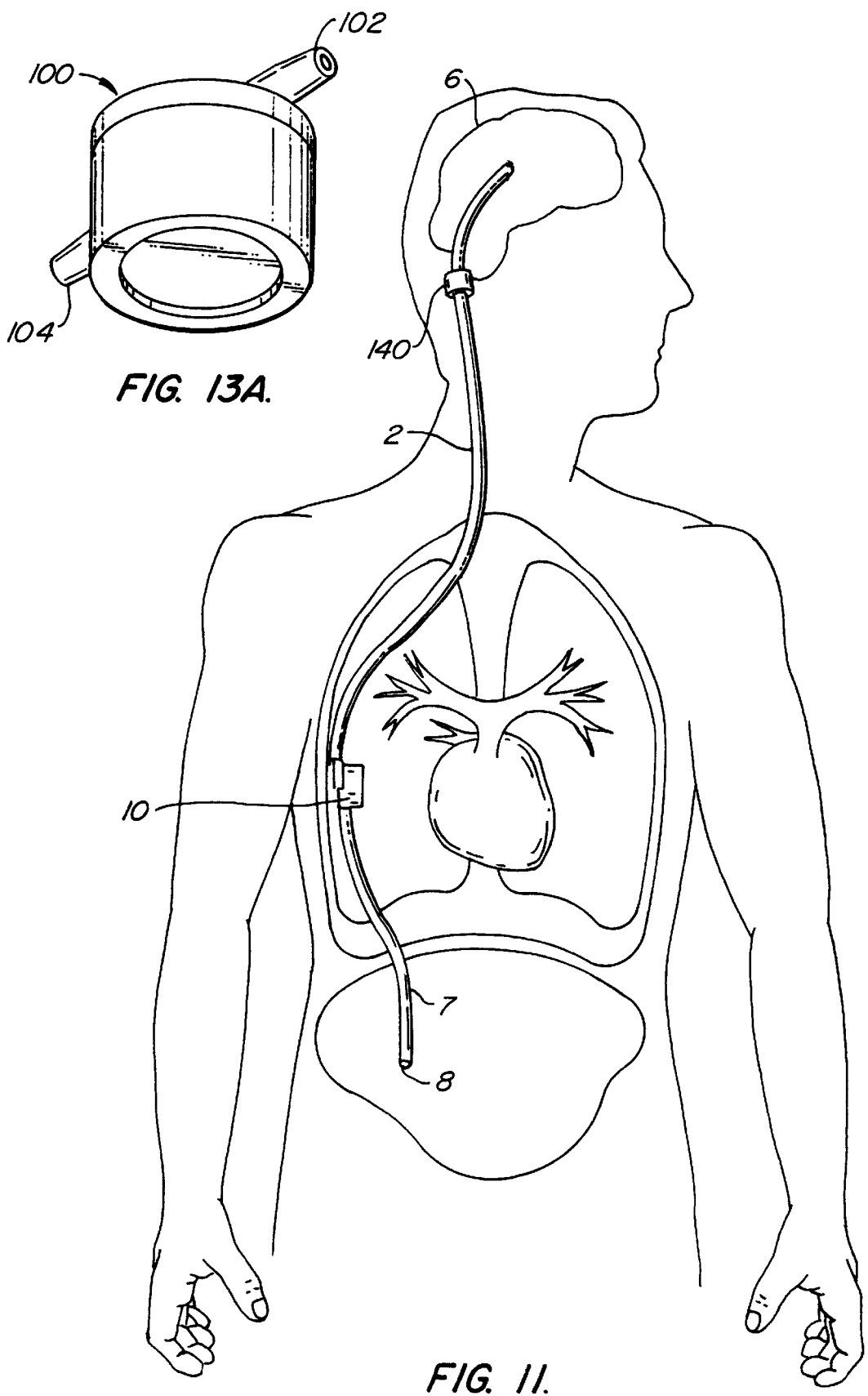
FIG. 11 shows another arrangement of the invention in which the flow rate control device is a pump powered by pressure changes within the patient.
FIG. 13A is perspective view of the pump shown in FIG. 11.

Conduit 2 has a second end portion having an outlet or discharge opening 8 external to the space within the patient's subarachnoid space 6 for draining cerebrospinal fluid to other body cavities. Thus, in the embodiments described below, the conduit's outlet opening is disposed in another portion of the patient's body such as in the peritoneal cavity as shown in FIG. 11, for example. It should be recognized, however, that the second end of the conduit may also be disposed transcutaneously to lie completely external to the patient's body so that the transported cerebrospinal fluid is completely removed from the patient. In this case, the conduit may be led subcutaneously from the head to the abdomen and exit transcutaneously from the abdomen.

The outlet or discharge portion of conduit 2 may, for example, be in the form of a conventional peritoneal catheter of the type used for peritoneal dialysis. Such catheters may be joined directly to the inlet portions of catheter 2, e.g. be joined directly to a ventricular catheter as discussed above. In a specific embodiment, as described in more detail below, a peritoneal catheter is joined to a flow control module which in turn is joined to the ventricular catheter in order to form a catheter system suitable for draining cerebrospinal fluid according to the methods of the present invention. The flow control module will control flow rate and will usually also control flow direction, i.e. permitting flow only in the direction from the subarachnoid space to the discharge location. Provision within the flow control module may also be made for detecting flow in order to assure that the system is operating properly after implantation.

Finally, in order to control the removal rate of cerebrospinal fluid from the patient, the preferred apparatus of this invention has a fluid flow rate control device 10 for controlling the flow rate of fluid through conduit 2 (optionally embodied in a flow control module as described above). When placed in the thoracic cavity (see FIG. 11), fluid flow rate control device 10 preferably is positioned in the lateral mid-thorax near the axillary line and preferably on the under surface of a rib. It is held in place with sutures to the periosteum. The flow rate control device may comprise a flow restrictor which limits the flow rate of cerebrospinal fluid to practice the method of this invention. The flow restrictor may be an element separate from the conduit or it might be made integral with the conduit, e.g. an integral orifice, a contiguous length of reduced diameter tubing, or other passive flow control element.

Figure 2:
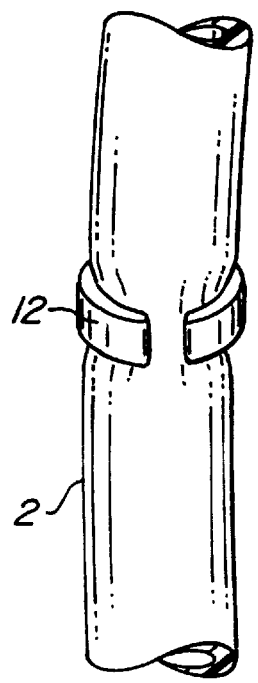
FIG. 2 shows an embodiment of this invention utilizing a resilient fluid conduit in combination with a clamp which sizes or constructs the lumen diameter of the conduit.
Figure 3:
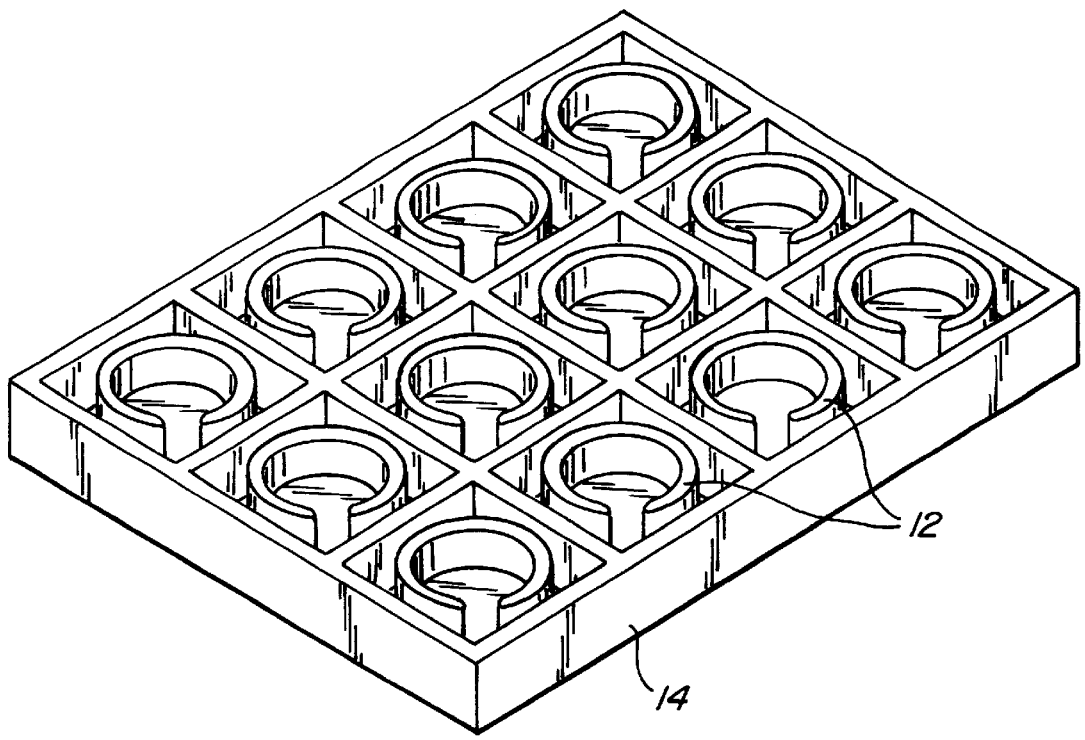
FIG. 3 shows a package containing a variety of clamps for use with the embodiment of the invention shown in FIG. 2.

FIG. 2 shows an embodiment of the invention in which conduit 2 is formed from resilient material, such as implant grade silicone or reinforced silicone tubing. In this embodiment, the flow rate control device is a clamp 12 attached to a portion of conduit 2 outside of the subarachnoid space 6, which has a split ring configuration and is preferably positioned near the outlet of conduit 2 which may be placed in the peritoneum, for example. Clamp 12, which is configured to constrict conduit 2 and the lumen formed therein, is preferably sufficiently rigid so as not to allow significant variance in conduit constriction when fluid pressure changes. However, clamp 12 is preferably sufficiently resilient to facilitate its placement around conduit 2. Clamp 12 may comprise or be made from materials such as polycarbonates, polystyrenes or stainless steels as would be apparent to one of ordinary skill in the art. The properties of other characteristic of the conduit and clamp are selected to provide predictable resistance to flow through the conduit lumen by creating a reduced flow region having a fixed diameter that does not change with time or fluid pressure. In this manner, an appropriate amount of cerebrospinal fluid flow from the space within the patient's subarachnoid space 6. The clamp preferably is positioned near the outlet of conduit 2 (e.g., within about 4 cm of the outlet) so that the surgeon may verify proper selection during implant by visualization of output.

In order to provide the physician with a range of conduit flow rate control, a variety of clamps may be provided, each having different durometers, shapes, sizes, and/or other characteristics. In general, the physician can determine the cerebrospinal fluid pressure when placing the conduit in a ventricle and, then, select a clip that provides the desired flow rate, which preferably is in the range of about 17 to 25 ml/hr, inclusive does not exceed 0.35 (which generally corresponds to a typical range for a rate of production of cerebrospinal fluid) at intraventricular pressures less than or equal to 15 cm $H_2O$. Each clamp may be packaged in a separate, flexible and sterile container or pouch, the clamps may be placed in a tray 14, having multiple receptacles, with or without the individualized containers described above. The clamps also could be assembled with one or more conduits into a kit for use by a physician during implant of the apparatus.

Figure 4:
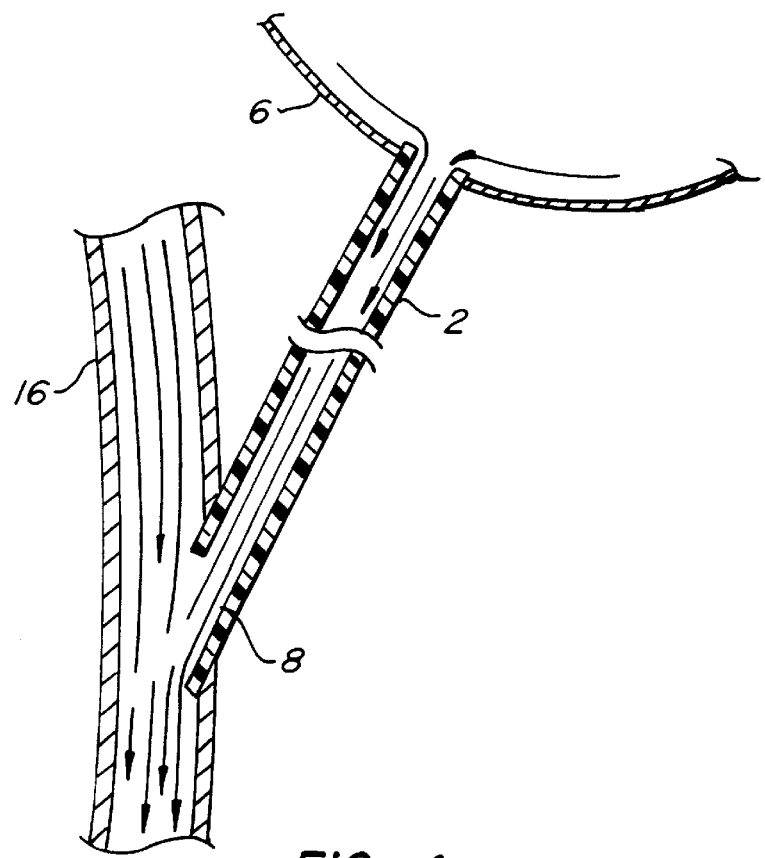
FIG. 4 shows a venturi powered flow arrangement according to one embodiment of this invention.

FIG. 4 shows an embodiment in which the fluid flow rate control device is a connection between the outlet opening 8 of conduit 2 and a fluid-carrying vessel 16 within the patent.

Vessel 16 could be a native vessel (such as a blood vessel, e.g., such as the subclavian vein) or an implanted vessel. In either case, the fluid flowing through vessel 16 creates a low pressure area (venturi) at outlet opening 8 of conduit 2. This low pressure area helps draw cerebrospinal fluid through conduit 2 at an appropriate rate. An active or passive flow restrictor may be used to limit the flow in such embodiments.

Figure 5A:
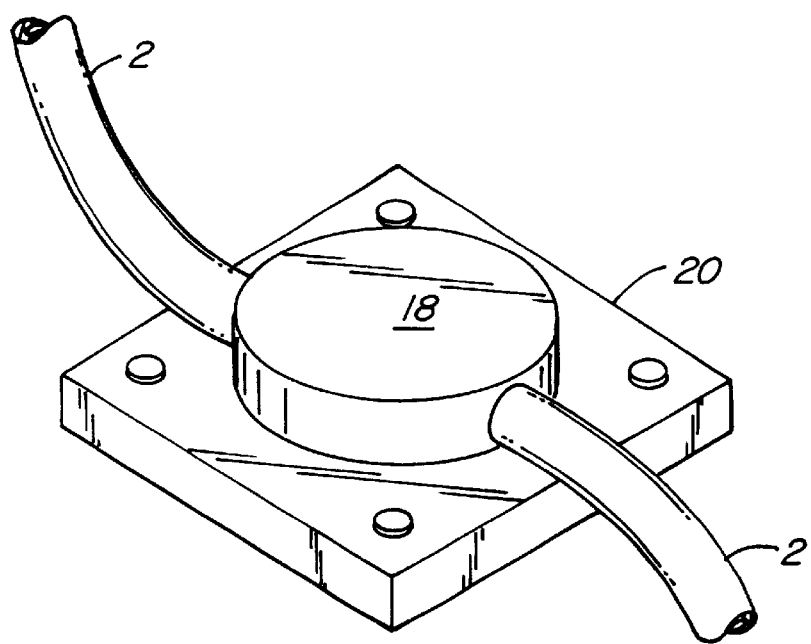
FIG. 5A shows an embodiment of the invention in which the fluid flow rate control device is a pump.
Figure 5B:
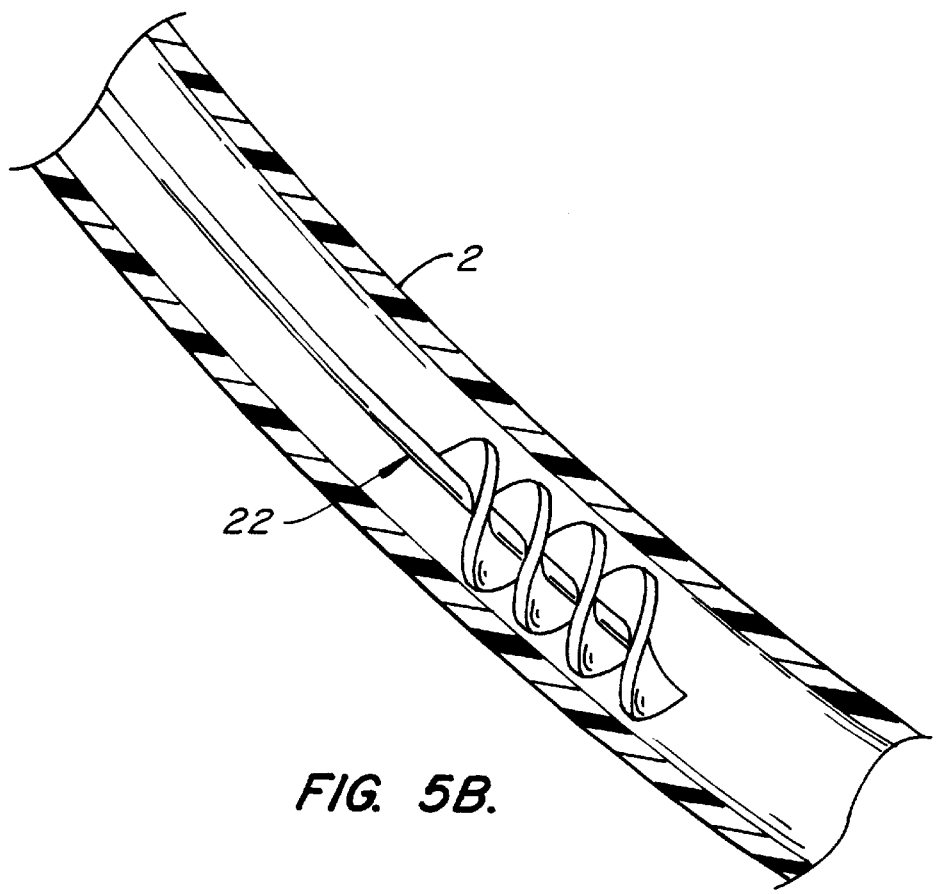
FIG. 5B shows an embodiment of the invention in which the fluid flow rate control device is a screw pump.

FIG. 5A shows an embodiment in which the fluid flow rate control device is an implantable pump 18 attached to conduit 2. Pump 18 may be a diaphragm pump, piston pump, rotor pump, peristaltic pump, screw pump, or any other suitable pump. The power source for pump 18 may be a battery or other energy storage device, such as a mechanical flywheel with self-winding operation. The pump also may be remotely operated as is known in the art. Pump 18 further may be operated continuously or periodically, either on demand or according to a schedule or program. Pump 18 may be mounted on a baseplate 20 which is adapted for attachment to a portion of the patient's anatomy. FIG. 5B illustrates a conventional screw pump arrangement where a screw shaft 22 is mounted for rotation within conduit 2. The drive may be positioned in a hermetically sealed package mounted to the conduit exterior and arranged within the thorax or peritoneum. The drive may be coupled to screw shaft 22 with a gear transmission as would be apparent to one of ordinary skill in the art. Other screw pump configurations also can be used such as those disclosed in U.S. Pat. No. 4,857,046 to Stevens et al. to U.S. Pat. No. 5,372,573 to Habib.

Figure 6:
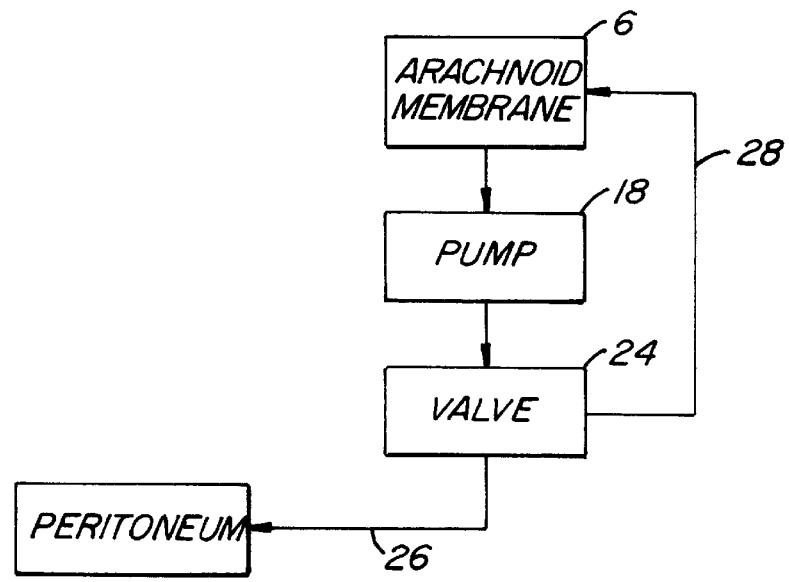
FIG. 6 diagrammatically shows an embodiment of the invention providing for recirculation of the patient's cerebrospinal fluid.

FIG. 6 diagrammatically shows an embodiment of the invention in which a return loop is provided. In this embodiment, the fluid flow rate control device includes a bidirectional valve 24 and a pump, such as a pump 18. The pump is coupled to conduit 2 to pump fluid therethrough and the valve is fluidly coupled to the pump. Valve 24 switches the effluent of the pump between a discharge line 26, which may form part of conduit 2, and a return line, 28. The discharge line may have an outlet located within the patient's body (e.g. it may be located in the peritoneum) or exterior to the patient. Return line 28 has an outlet adapted for being located within the patient's subarachnoid space (e.g., in one of the lateral ventricles as discussed above). In this embodiment, the pump is operated substantially continuously to remove cerebrospinal fluid from, for example, the ventricles. Valve 24 is switched between lines 26 and 28 to maintain proper pressure of the patient's subarachnoid space. Valve 24 may be operated on a time basis or on a demand basis, e.g., based on sensed cerebrospinal fluid pressure. Generally, cerebrospinal fluid removal may be undesirable at fluid pressures below about 6 cm $H_2O$. A pressure transducer may be used to sense that pressure and control valve 24 to control the flow rate of cerebrospinal fluid as will be described below with reference to FIG. 7.

Referring to FIG. 7, a pressure transducer 30 may be arranged on the exterior of conduit or conduit 2 in the vicinity of the tip of inlet portion 3 for sensing cerebrospinal fluid pressure. Transducer 30 may be selected to send a signal to valve 24 through leads 32 in response to sensing a signal below a threshold value of 66 cm $H_2O$. The valve may include a solenoid for switching the valve to the recirculation position discussed above in response to receiving the signal from the transducer. Leads 32 may be embedded in conduit 2 or otherwise coupled to the conduit and extend along the conduit to couple the transducer to the valve control mechanism or solenoid as would be apparent to one of ordinary skill. For example, leads 32 may be placed on the exterior surface of conduit 2 and thin walled shrink tubing placed around conduit 2 and leads 32 to embed the leads between the conduit and shrink tubing and secure them in position.

Figure 8A:
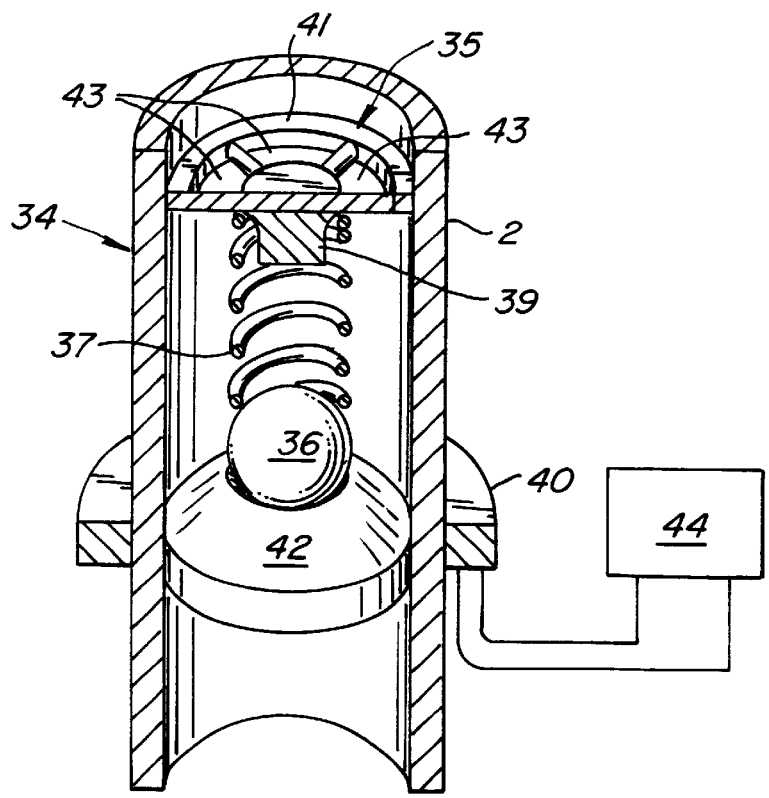
FIGS. 8A and 8B show an embodiment of the invention in which the fluid flow rate control device is a valve.
Figure 8B:
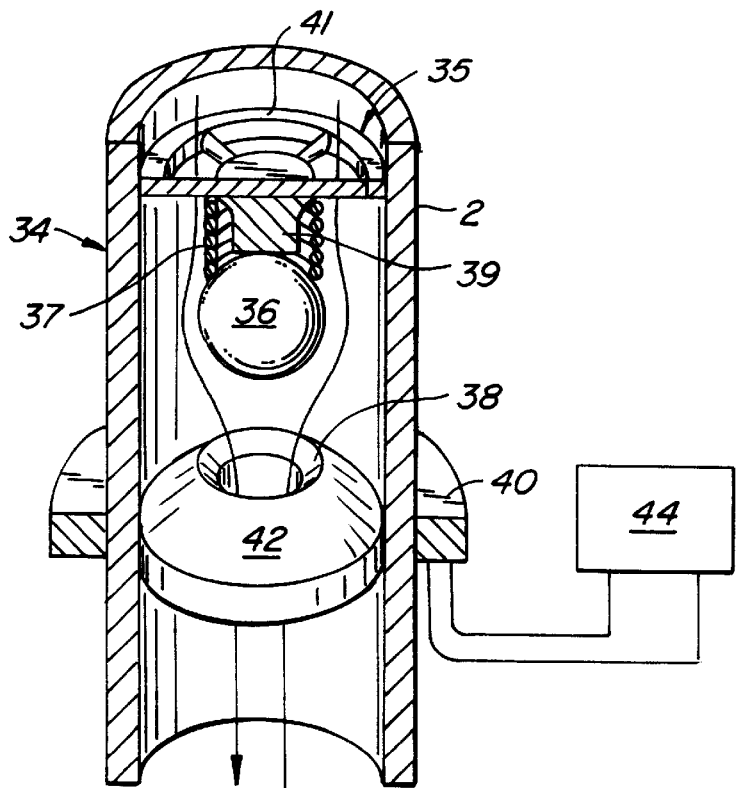

FIGS. 8A and 8B show an embodiment of the invention in which the fluid flow rate control device is a ball valve 34 which generally includes a valve member 36, valve seat 38 and valve member retaining mechanism 35. Retaining mechanism 35 limits upstream movement of valve member 36 and may comprise a coil spring 37 which may be held in place by a post 39 as shown in FIGS. 8A and 8B. Post 39 may be secured to a structure, such as structure 41, which, in turn, is secured to the inner wall of conduit 2. Structure 41 includes openings, such as openings 43 formed between circumferentially spaced spokes 45, for allowing fluid flow therethrough. Structure 41 may be annular with the line along the cross-sectioned portion in FIGS. 8A and 8B corresponding an axis of symmetry so that the unshown portion is a mirror image of what is shown. Accordingly, structure 41 may have a wagon wheel configuration as shown in FIGS. 8A and 8B. Spring 37 maintains valve member 36, seated until the valve is actuated as will be described below.

Valve member 36 is a ferromagnetic sphere formed, e.g., from stainless steel. The ferromagnetic material may be biocompatible material (e.g., stainless steel), or it may comprise nonbiocompatible material which may be encapsulated in a biocompatible material (e.g., a relatively inert polymer such as polytetrafluoroethylene). As shown in FIG. 8A, valve member 36 rests on a valve seat 38 to prevent fluid flow through conduit 2. Referring to FIG. 8B, valve member 36 may be lifted off seat 38 through the use of an external ring shaped magnet 40 which is energized by power source 44. Power source 44 can be coupled to a pressure sensor such as pressure transducer 30 described above and programmed so that the magnet is deenergized when the cerebrospinal fluid pressure within the subarachnoid space drops below 6 cm $H_2O$. Although a particular valve actuating member is shown, it should be understood that other actuating mechanisms may be used. For example, valve member 36 may be lifted off seat 38 through the operation of solenoid coils (not shown) within the seat member 42. Valve 34 may be operated on a time schedule or on demand to drain a specified volume of cerebrospinal fluid from the space within the patient's subarachnoid space.

Power source 44 may be coupled to a pressure transducer that is coupled to the conduit as described above with reference to FIG. 6. Similarly, the pressure transducer may be selected to send a signal to the power source indicative of a first condition where sufficient cerebrospinal fluid pressure is present and a signal indicative of a second condition where insufficient pressure is present when the cerebrospinal fluid pressure is below about 6 cm $H_2O$. The power source would include a circuit for actuating the magnet when the signal indicative of the first condition is received and deactuating the magnet when the signal indicative of the second signal is received.

Figure 9:
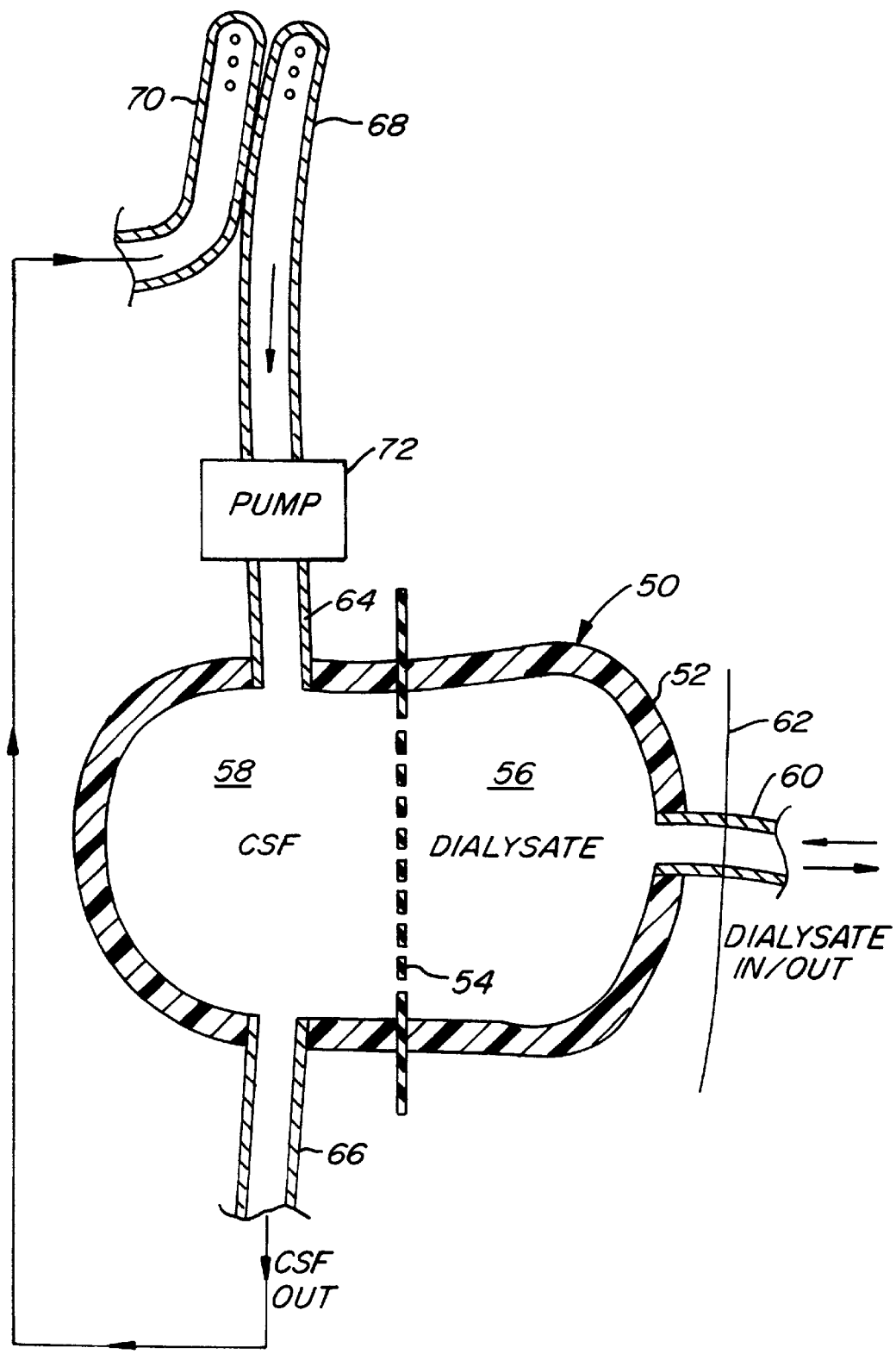
FIG. 9 shows a further embodiment of the invention including dialysis apparatus to remove substances from cerebrospinal fluid.

Referring to FIG. 9, a further variation of the invention is shown. As an alternative to the filtering operation described in Matkovich U.S. Pat. No. 5,334,315, toxins may be removed from the patient's cerebrospinal fluid through dialysis.

FIG. 9 shows a cerebrospinal fluid treatment circuit including dialysis apparatus 50, which preferably is adapted for implantation within the patient. Apparatus 50 may comprise a bag or flexible container 52 as shown in FIG. 9. Bag or container 52 is biocompatible and may be made of silicone or other suitable materials as would be apparent to one of ordinary skill in the art. A micropourous membrane 54, supported in support member 44 divides the container into two chambers: a dialysate chamber 56 and a cerebrospinal fluid chamber 58. Member 54 preferably has a port size <0.2 micron to provide a biologic barrier and may comprise micropourous polytetrafluoroethylene, silicone or polypropylene, for example. A dialysate inlet connector tube 60 similar in construction to those found in conventional peritoneal dialysis systems is in fluid communication with dialysate chamber 56 and may extend through the patient's abdominal wall, designated with reference numeral 62, when apparatus 50 is implanted within the patient's peritoneal cavity. The dialysate chamber preferably has about a one to two liter capacity. The dialysate in chamber 56 may be exchanged or supplemented with fresh dialysate on a daily or monthly basis or some other interval depending on the rate of formation of the toxic substances in the cerebrospinal fluid.

Container 52 also includes an inlet and outlet fluidly coupled to conduits 64 and 66, which may form port of or be extensions to conduit 2 discussed above. Toxic or putative chemicals in the cerebrospinal fluid move into the dialysate through diffusion. This diffusion is a function of the toxic chemical concentration gradient that exists between the cerebrospinal fluid and the dialysate which at t=0 has none of toxic/putative chemicals in solution. The concentration gradient between these two compartments will over time go to zero. Prior to this point the dialysate may be flushed out or exchanged.

Treated cerebrospinal fluid can flow out of chamber 58 through conduit 66. The fluid is then recirculated back to one of the lateral ventricles, for example, through conduit 66. The end portions 68 and 70 of conduits 64 and 66 are configured and adapted for placement in the subarachnoid space. End portion 68 may be positioned to remove cerebrospinal fluid from one lateral ventricle and end portion 70 positioned to return the treated fluid to the other lateral ventricle. Each end portion 68 and 70 may be constructed the same as inlet end portion 3 shown in FIG. 7.

A pump 72, which may be any of the pumps discussed with reference to pump 18, may be provided in or coupled to either conduit 64 or 66 or be integrated in container 52 to ensure adequate flow rate of cerebrospinal fluid. However, it should be noted that the pump preferably is arranged upstream of chamber 56 to avoid the possibility of air being drawn in the apparatus if dialysate chamber 54 were to become less than full with dialysate. Conduits 64 and 66 may be separate members preferably close to the inlet of pump 72.

The inner wall of the portion of container 52 that forms chamber 56 may be coated with antibodies specific to particular agents present in the cerebrospinal fluid. That is, the antibodies may be linked or bound to the inner wall of chamber 56 so that they may capture putative toxic chemicals and draw them out of solution, keeping the driving concentration gradient between cerebrospinal fluid and dialysate high. Alternatively, the antibodies may be bound to beads, strands or other structures which may be periodically introduced into and retrieved from the dialysate chamber through dialysate port 60.

Figure 10A:
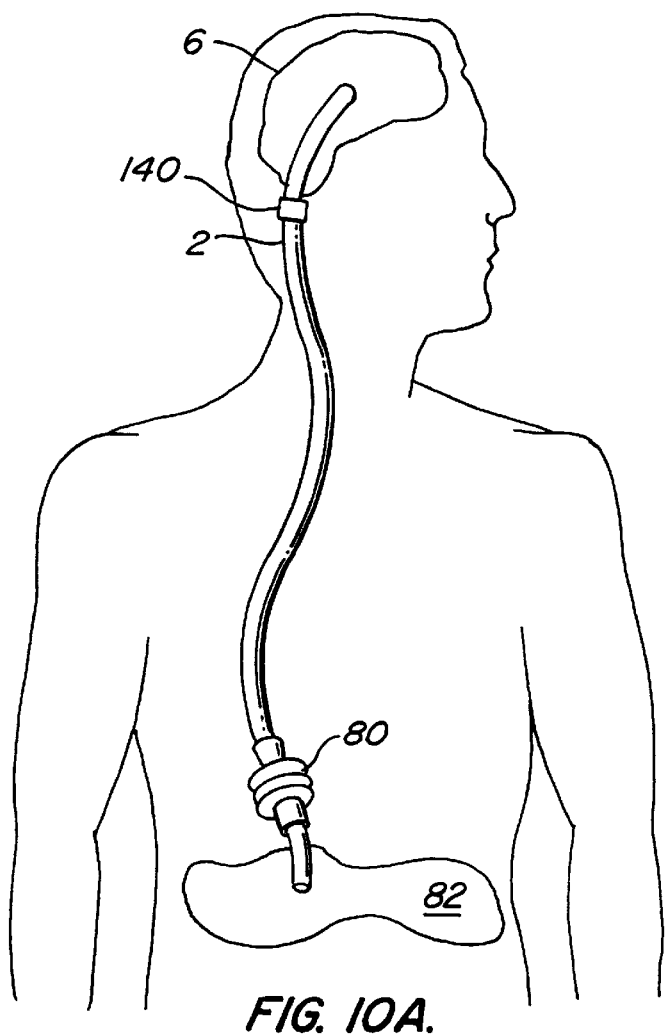
FIGS. 10A, 10B, 10C and 10E show an embodiment of the invention in which the flow rate control device is a bellows pump powered by the patient.
Figure 10B:
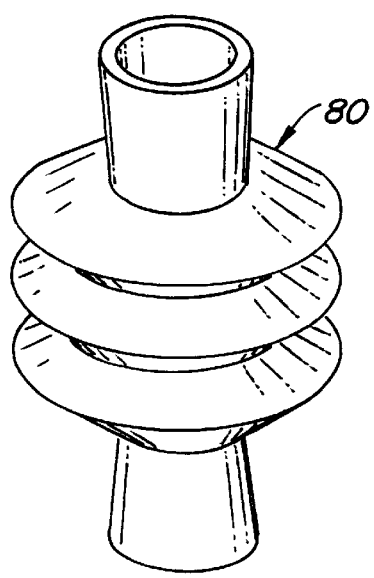
Figure 10C:
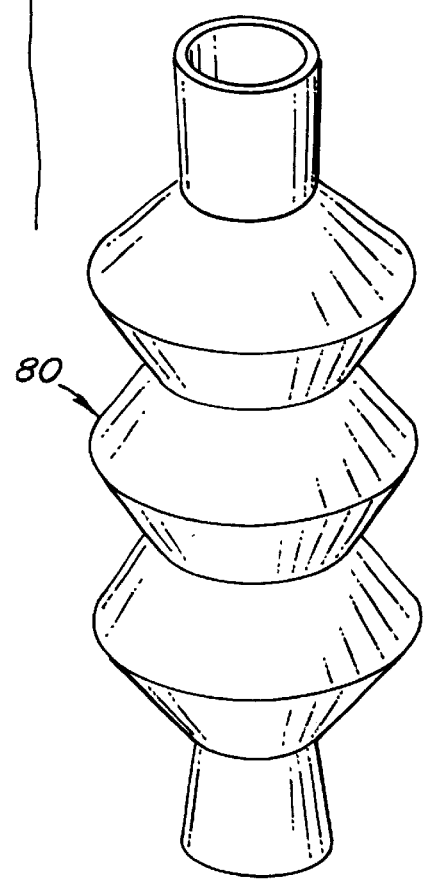

The flow-rate control device of the invention also may be a pump powered by the patient without the use of any external or internal stored energy source. Referring to FIG. 10A, an embodiment of the invention in which the flow rate control device is a bellows-type pump 80 powered by the motion of the patient's diaphragm 82 is shown. Pump 80 generally includes a check valve to prevent flow of fluid back into the space within the patient's subarachnoid space and an outlet valve as will be discussed in more detail below. One end of the valve is fixed to the diaphragm and the other to some anatomy of the patient, e.g., a rib, so that when the diaphragm moves, the pump moves between the positions shown in FIGS. 10B and 10C.

Figure 10D:
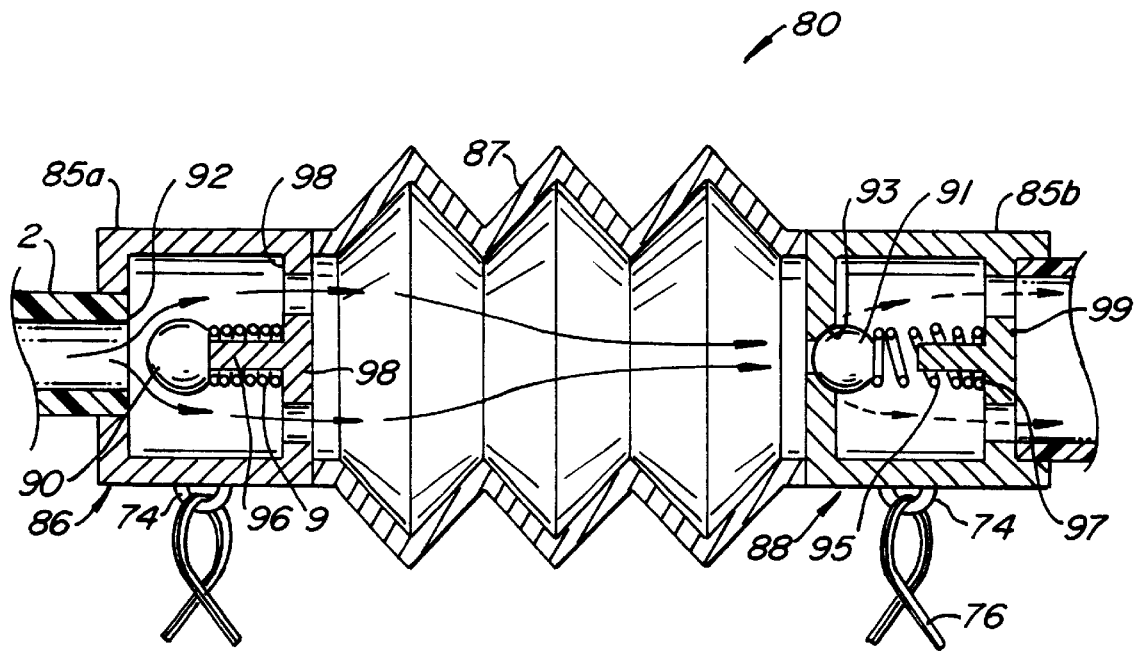
FIG. 10D is a sectional view of an embodiment of the patient driven bellows pump illustrated in FIGS. 10A, 10B and 10C.

Bellows pump 80 may be constructed as shown in FIG. 10D where the pump is illustrated in section. Bellows pump 80 generally includes end portions 85a and 85b and bellows portion 87. End portions 85a and 85b may include loops 74 to receive sutures 76 for securing the valve to the anatomy as discussed above. End portions 85a and 85b also form the housings for inlet and outlet valves 86 and 88. Valves 86 and 88 include spherical valve members 90 and 91 that are biased against valve seats 92 and 93 by coil springs 94 and 95. The coil springs surround spring support posts 96 and 97 which extend from or are secured to post support structures 98 and 99. Structures 98 and 99 are perforated to allow cerebrospinal fluid flow therethrough. Support posts 96 and 97 and structures 98 and 99 may be configured like structure 35 shown in FIGS. 8A and 8B.

A check valve 140 (see, e.g., FIGS. 10A and 14) may form part of the flow rate control device and may be provided to maintain the desired physiologic conditions within the subarachnoid space. Valve 140 preferably is selected to close conduit 2 and prevent fluid flow therethrough when cerebrospinal fluid pressure within the subarachnoid space drops below 6 inches $H_2O$, for example. Valve 140 preferably is positioned adjacent and external to the skull.

Figure 14:
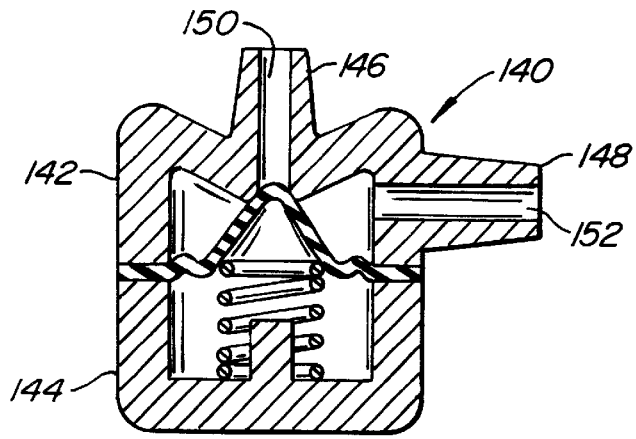
FIG. 14 is a cross-section of the inlet valve at the upstream end of the apparatus diagrammatically shown in FIG. 11.

Referring to FIG. 14, check valve 140 comprises an upper housing portion 142 and lower housing portion 144. Upper portion 142 further includes inlet portion 146 and outlet portion 148 which define inlet passages 150 and 152. Inlet and outlet portions 146 and 148 preferably are arranged with their central axes being generally perpendicular to one another as shown in FIG. 14 to facilitate implantation below the dermis. Diaphragm 154, which may comprise, for example, any of the materials described above with reference to diaphragm 118, is positioned between upper and lower portions 142 and 144, forms first chamber 156 and second chamber 158 and provides a seal therebetween. Diaphragm 154 includes a conical portion 160 for fitting within and sealing inlet passage 150 as shown in FIG. 14. Diaphragm 154 is biased toward the position shown in FIG. 14 by coil spring 162, which is positioned around post 164. Coil spring 162 is selected to allow diaphragm 154 to move away from inlet passage 150, thereby allowing cerebrospinal fluid to flow through inlet passage 150 and be discharged from outlet passage 152, when the cerebrospinal fluid pressure exceeds about 6 cm $H_2O$. Upper and lower portions 142 and 144 may be generally annular as shown in the drawings.

Returning to FIG. 10D, inlet valve 86 is a check valve and prevents backflow of cerebrospinal fluid from the pump. It is constructed to open at very low pressures (e.g., it may be designed to open at 5–10 cm $H_2O$). Outlet valve 88 is designed to have a cracking pressure greater than or equal to the maximum cerebrospinal fluid pressure within the subarachnoid space (the fluid pressure within this space typically ranges from about 1 to 6 cm $H_2O$). Thus, in this example the cracking pressure is designed to be greater than or equal to 15 cm $H_2O$. When valve 140 is set to open 6 cm $H_2O$, as discussed above, bellows pump 80 is configured to increase the fluid pressure in the bellows to a minimum of 15 cm $H_2O$ during contraction to crack the outlet valve.

These design parameters, including valve 140 being designed to open at pressures greater than or equal to 6 cm $H_2O$, facilitate drainage only when the patient is lying down. Valve 140 typically will see pressures less than 6 cm $H_2O$ when the patient stands and close in response to such pressures. Although particular valve cracking pressures have been described, other preselected values may be used for operation at different postures of the patient where different intraventricular or column height pressures occur.

In operation, inlet valve 86 is open and outlet valve 88 closed when the bellows is expanded as shown in FIG. 10D and the inlet valve is fluidly coupled to cerebrospinal fluid within the subarachnoid space. Inlet valve 86 closes and outlet valve 88 opens when the bellows contracts and the cracking pressure for the outlet valve is attained.

Figure 10E:
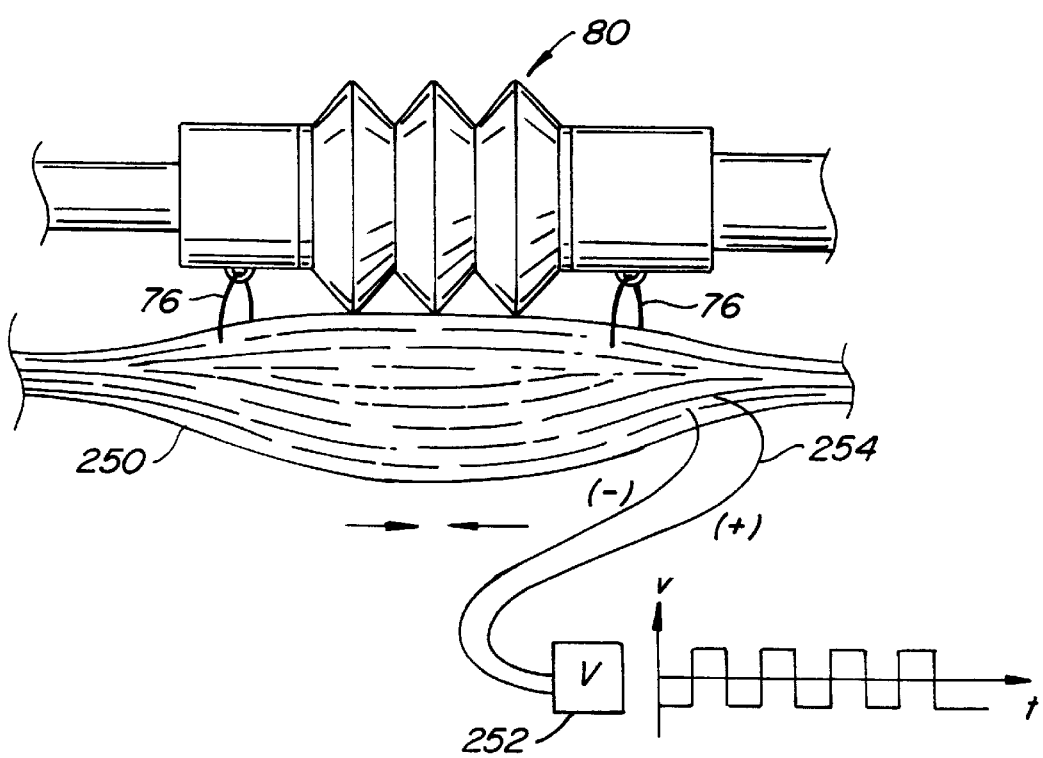

Other structures such as muscles can be used to actuate the bellows pump as well if they allow a reasonably regular or controllable frequency of action. Another embodiment of the invention where the bellows is attached to is an isolated muscle group is shown in FIG. 10E. The muscle contraction frequency is controlled by an implant electronic stimulator as diagrammatically shown in the drawing. The bellows pump may be identical in construction to bellows pump 80 described with reference to FIG. 10D as indicated in the drawing and may be secured to muscle 250 with sutures 76. Electronic muscle stimulator implant 252 may be electrically coupled to muscle 250 with leads 254 which may be sutured to the muscle as is done in implantable defibrillator placement. The sutures are made sufficiently taut to have the pump contract with the muscle. Stimulator 252 may comprise a power source programmed to deliver <1 volt (at negligible current) to effect muscle contraction as would be apparent to one of ordinary skill in the art. The frequency of excitation preferably is predetermined and may correspond to 12 to 20 cycles per minute (which corresponds to a typical breathing rate) or it may vary from that range. The stimulator preferably is designed to operate only when the patient is lying down and may include known level detection circuitry to trigger operation. Transducer 30 also may be incorporated in this embodiment to shut down stimulator 252 when the fluid pressure within the subarachnoid space is less than 6 cm $H_2O$ or control excitation frequency depending on pressure greater than or equal to 6 cm $H_2O$.

Figure 12A:
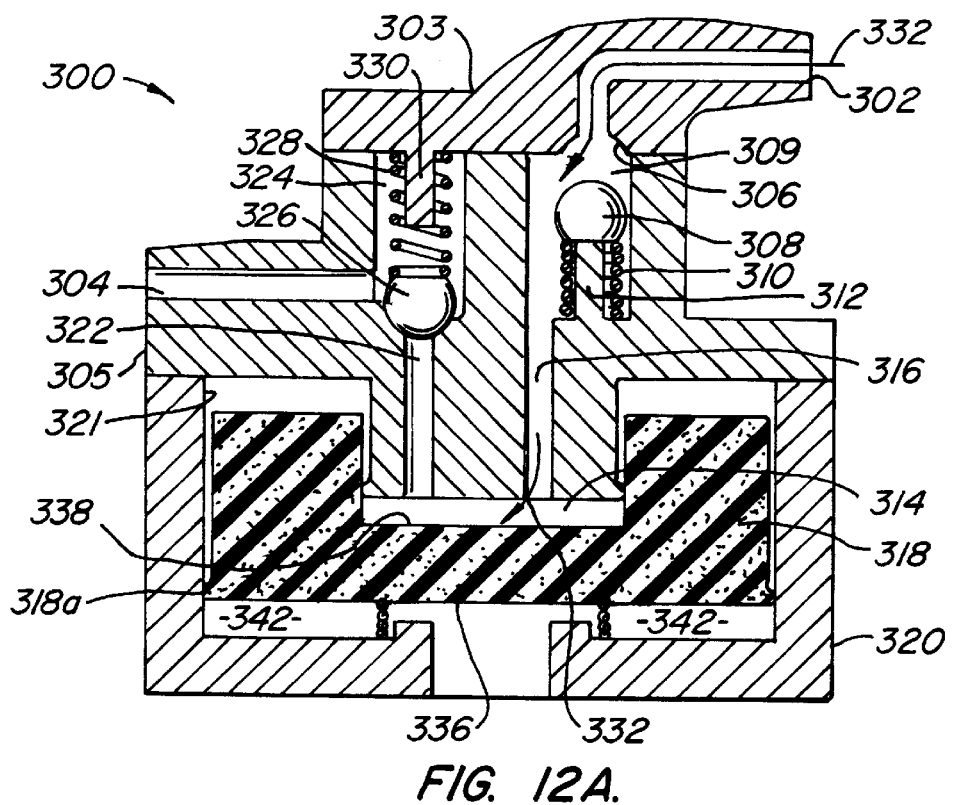
FIG. 12A is a sectional view of a pressure driven pump constructed according to the present invention in an intake cycle.
Figure 12B:
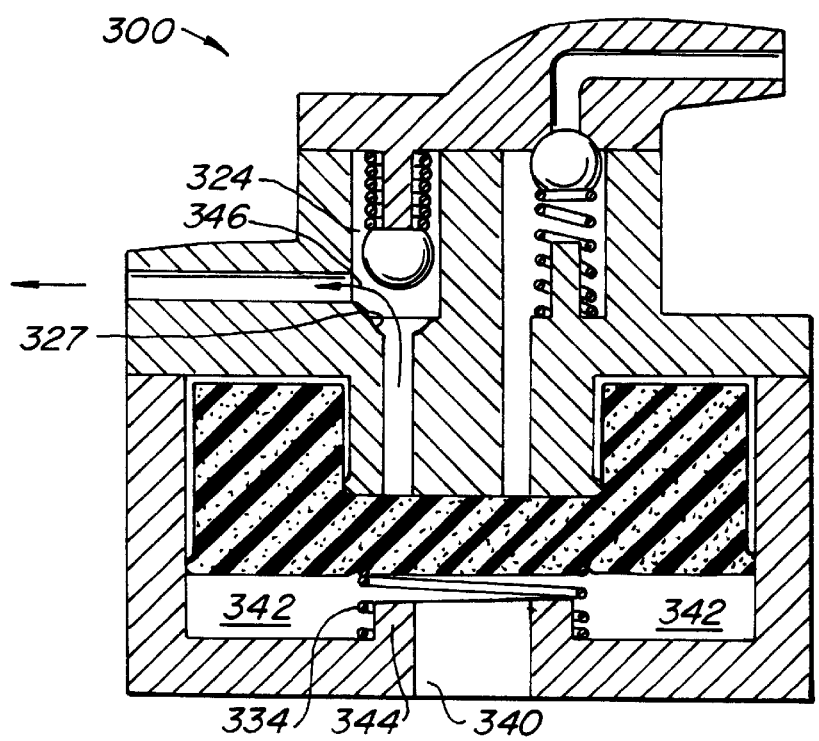
FIG. 12B shows the pump of FIG. 12A during discharge.

Referring to FIG. 11, another flow rate control device constructed according to the invention is shown. According to this embodiment, the flow rate control device responds to pressure changes within the patient. The flow rate control device may, for example, be driven by pressure changes in the thoracic cavity. It may be coupled to the periosteum in the same manner as described above with reference to FIG. 1 and the outlet 8 of conduit 2 positioned in the peritoneal cavity. Flow rate control device 10 (FIG. 11) may be a piston pump as shown in FIGS. 12A and 12B and designated with reference numeral 300. As in the foregoing and following embodiments, a diaphragm pump may be used in conjunction with a check valve such as check valve 140 (FIG. 14).

Piston pump 300 (FIG. 12A) comprises an inlet 302 passage formed in upper housing portion 303 of the pump and an outlet passage 304 formed in the pump's middle housing portion 305. Middle portion 305 defines in part inlet chamber 306 in which resides first valve member 308, which is in the form of a spherical ball. Valve member 308 is biased against valve seat 309 which is formed in upper portion 303 in the downstream end portion of inlet passage 302. Valve member 308 is biased toward valve seat 309 by coil spring 310 which surrounds and is supported by post 312.

Inlet chamber 306 is fluidly coupled to piston chamber 314 through passage 316. Piston chamber 314 is formed by the recess in piston 318 and a portion of middle portion 315 that extends therein as shown in FIG. 12A. Piston chamber 314 is sealed from the environment, such as that found in the thoracic cavity, by piston 318 (which may be generally cylindrical) and is sealingly coupled to an inner wall 321 of lower housing portion 320 (which may be annular), as shown in FIGS. 12A and 12B. The seal may be formed by raised portion or rib 318a that extends from piston 318 or an O-ring, for example. Lower housing portion 320, in turn, is secured to middle portion 305 by conventional means such as welding. Passage 322 fluidly couples piston chamber 314 to outlet chamber 324 when valve member 326 is in the position shown in FIG. 12B. More specifically, second valve member 326, which is in the form of a spherical ball, is biased against valve seat 327 by coil spring 328 which, in turn, is supported by post 330. As shown in the drawings, inlet and outlet chambers 306 and 324 are fluidly coupled to inlet and outlet passages 302 and 304. Piston 318 may comprise an elastomeric material, such as polytetrafluoroethylene, or high durometer silicone.

The pressure in the thoracic cavity, which, as noted above, varies on each breath, is the driving force for piston pump 300. When the thoracic cavity pressure is low (e.g., at about −8 cm $H_2O$) piston 318 is drawn out and valve member 308 retracts from valve seat 307 as shown in FIG. 12A. In this position, cerebrospinal fluid flows into inlet passage 302, through inlet chamber 306 and into piston chamber 314 as indicated by arrows 332. When the pressure in the thoracic cavity increases to about −5 cm $H_2O$, return spring 334 forces or urges piston 318 inwardly to a closed position such that second valve member 326 moves away from valve seat 327, while first valve member 308 returns to valve seat 309 as shown in FIG. 12B. In this position, cerebrospinal fluid, designated with reference arrow 346, is discharged from piston chamber 314, through outlet chamber 324 and out from outlet 304 to conduit 2 (FIG. 11).

Referring to FIGS. 12A and 12B the inlet valve, which includes ball 306, is a check valve and prevents backflow of cerebrospinal fluid from the pump (i.e., it prevents flow in the upstream direction). It is constructed to open at very low pressures (e.g., it may be designed to open at 1–6 cm $H_2O$). The outlet valve, which includes ball 326, is designed to have a cracking (opening) pressure greater than or equal to the maximum cerebrospinal fluid pressure within the subarachnoid space (the fluid pressure typically ranges from about 5 to 15 cm $H_2O$). Thus, in this example the cracking pressure is designed to be greater than or equal to 15 cm $H_2O$. When valve 140 is set to open at 6 cm $H_2O$, as discussed above, the piston and return spring 334 are configured to increase the fluid pressure in chamber 316 to a minimum of 15 cm $H_2O$ during compression to crack the outlet valve. The pump also may be designed to accommodate the relatively low pressures typically present in the thoracic cavity. The pressure in the thoracic cavity changes from about −5 to about −8 cm $H_2O$ during normal breathing. In view of this relatively low pressure change of about 3 cm $H_2O$, the piston preferably is designed to amplify the pressure available in the thoracic cavity to allow the piston to be drawn backwards and complete its outward stroke. This amplification may be about 3 to 5 fold and may be accomplished by providing an outer piston surface 336 with an area of about 3 to 5 times that of the inner working surface 338 of piston 318. As can be readily seen in FIG. 12B, outer piston surface area 336 is exposed to the environment through opening 340 and space 342 formed around and above coil support ring 344 in lower housing portion 320. These design parameters, including valve 140 being designed to open at pressures greater than or equal to 6 cm H₂O, facilitate drainage only when the patient is lying down. It should be noted, however, that other cracking pressures may be used, for example, to facilitate operation when the patient assumes other postures as discussed above with reference to bellows pump 80.

Figure 13B:
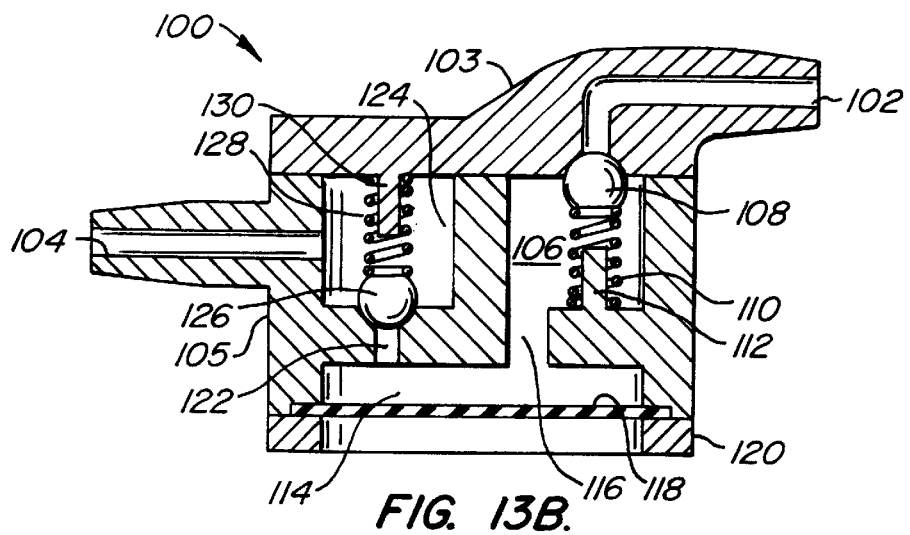
FIG. 13B is a transverse section of the pump shown in FIG. 12 diagrammatically showing inlet and outlet valves that may be incorporated therein.

In another embodiment of the invention, the flow rate control device may be a diaphragm pump such as diaphragm pump 100 illustrated in FIGS. 13A–13D. Referring to FIG. 13B, diaphragm pump 100 comprises an inlet passage 102 formed in upper housing portion 103 of the pump and an outlet passage 104 formed in the pump's middle housing portion 105. Middle portion 105 defines inlet chamber 106 in which resides first valve member 108, which is in the form of a spherical ball. Valve member 108 is biased against valve seat 109 which is formed in upper portion 103 in the downstream end portion of inlet 102. Valve member 108 is biased toward valve seat 109 by coil spring 110 which surrounds and is supported by post 112.

Inlet chamber 106 is fluidly coupled to diaphragm chamber 114 through inlet passage 116. Diaphragm chamber 114 is sealed from the environment through diaphragm 118 which is secured in place by generally ring shaped member 120. Ring shaped member 120, in turn, is secured to middle portion 105 by conventional means such as welding. Passage 122 fluidly couples diaphragm chamber 114 to outlet chamber 124 when valve member 126 is in the position shown in FIG. 13D. More specifically, second valve member 126, which is in the form of a spherical ball, is biased against valve seat 127 by coil spring 128 which, in turn, is supported by post 130. As shown in the drawings, inlet and outlet chambers 106 and 124 are fluidly coupled to inlet and outlet passages 102 and 104.

Figure 13C:
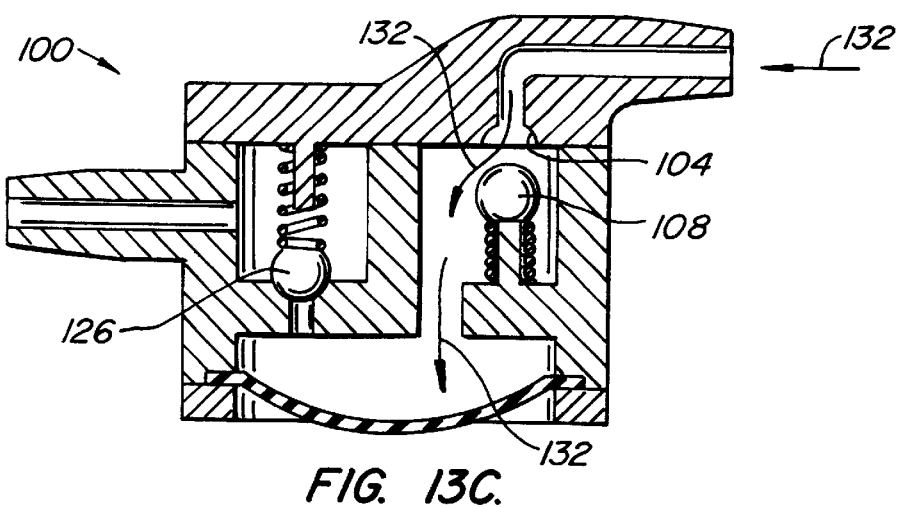
FIG. 13C shows the pump of FIG. 13A during intake.
Figure 13D:
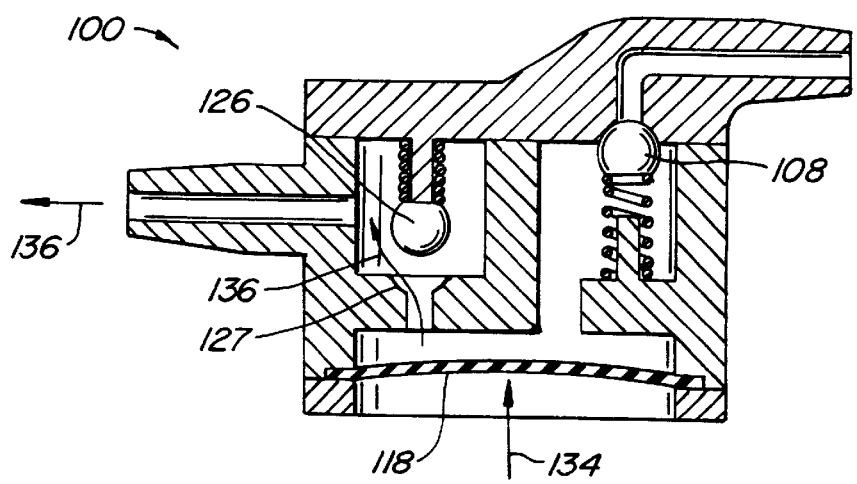
FIG. 13D shows the pump of FIG. 13A during discharge.

As with piston pump 300, the pressure in the thoracic cavity is the driving force for diaphragm pump 100. When the thoracic cavity pressure is low as compared to the pressure in chamber 114, diaphragm 118 is drawn out and valve member 108 retracts from valve seat 107 as shown in FIG. 13C. In this position, cerebrospinal fluid flows into inlet passage 102, through inlet chamber 106 and into diaphragm chamber 114 as indicated by arrows 132. When the pressure in the thoracic cavity increases such that it is greater than the pressure in chamber 114, the thoracic cavity pressure, generally indicated with reference numeral 134, forces diaphragm 118 inwardly such that second valve member 126 moves away from valve seat 127, while first valve member 108 returns to valve seat 107 as shown in FIG. 13D. In this position, cerebrospinal fluid is discharged from diaphragm chamber 114, through outlet chamber 116 and out from outlet 104 to conduit 2 (FIG. 11). As noted above, a check valve, such as check valve 140 may form part of the flow rate control device to maintain the desired physiologic conditions within the subarachnoid space. The pump inlet valve, outlet valve and diaphragm may be constructed according to the descriptions provided above with reference to the bellows and piston pump embodiments. The diaphragm also may be modified to accommodate relatively low pressure changes in the thoracic cavity.

Figure 15:
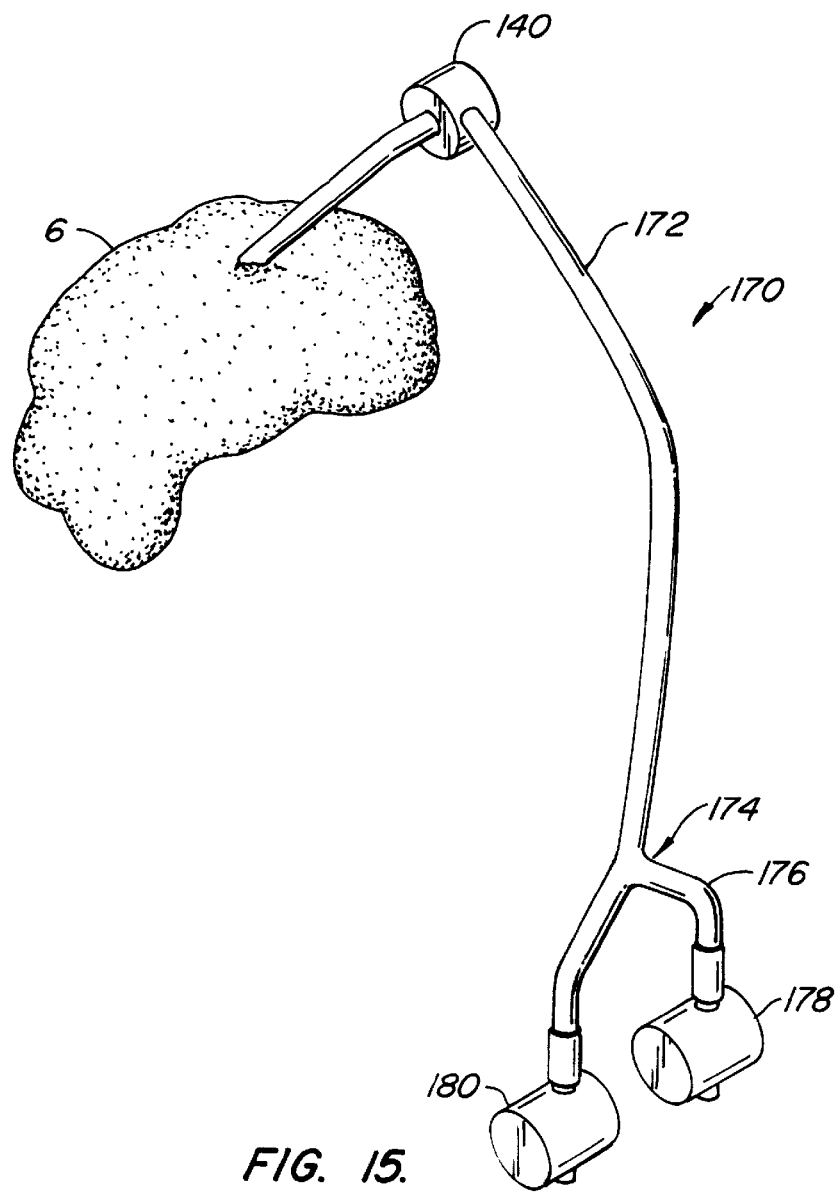
FIG. 15 is a perspective of a further embodiment of the invention for accommodating changes in pressure head. The inlet valve in the vicinity of the upstream end of the apparatus may be the same as in FIG. 14.

Referring to FIG. 15, a further embodiment of the invention is shown. Cerebrospinal fluid removal apparatus 170 generally comprises a conduit 170, which is the same as conduit 2 described above with the exception of having a bifurcated downstream portion 174. Bifurcated portion 174 includes parallel branches 176 that are coupled to valves 178 and 180, which, at least in part, form another fluid flow rate control device. The upper portion of conduit 172 is adapted for placement within the subarachnoid space 6 of the patient and may be configured like portion 3 of conduit 2 as shown in FIG. 7. Valves 178 and 180 are the same with the exception that they are constructed to be actuated at different pressures. Accordingly, a description of only one of the valves is provided below for purposes of simplification.

Figure 16:
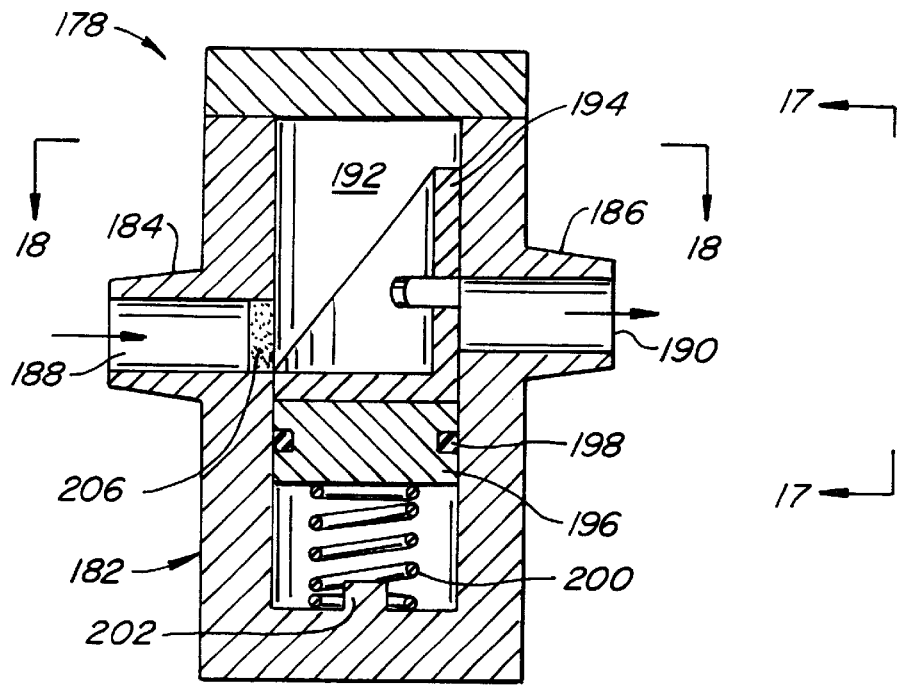
FIG. 16 is a cross-section of one of the downstream valves shown in FIG. 15. The downstream valves illustrated in this figure have the same construction with the exception of having different spring rates.

Referring to FIG. 16, valve 178 includes a housing 182 which may have a one-piece construction or an upper and lower portion as shown in the drawings. Housing 182 includes an inlet portion 184 and an outlet portion 186 defining inlet and outlet passages 188 and 190. Housing 182 further defines chamber 192 in which the valve member 194 is slidably positioned and supported on piston 196. Piston 196 is sized to slide along the inner wall surface that defines chamber 192. Piston 196 includes a circumferential groove in which an elastomeric ring 198 is placed. The elastomeric ring insures that the space in which valve member 194 is positioned is sealed from the space below piston 196. A coil spring 200 is positioned around post 202 for urging piston 196 and, thus, valve member 194 in an upward direction.

Figure 17:
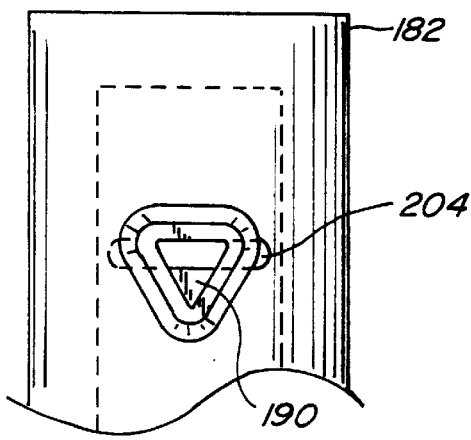
FIG. 17 is a side elevation of the valve shown in FIG. 16 as designated by line 17—17.
Figure 18:
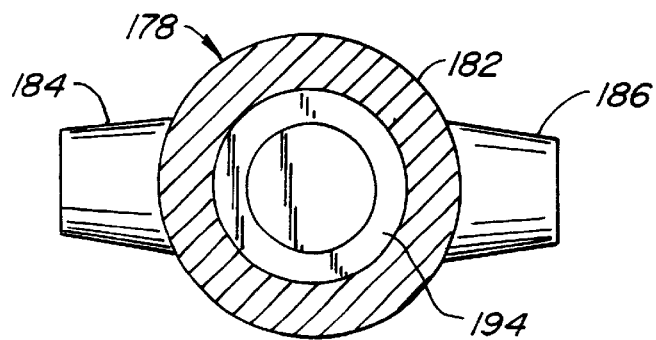
FIG. 18 is a sectional view of the valve shown in FIG. 17 taken along line 18—18.

Valve member 194 generally has a beveled cylindrical configuration (see FIGS. 16 and 18) and includes a slot 204 for fluidly coupling inlet passage 188 with outlet passage 190. Slot 204 is shown having a major axis and minor axis with the major access generally perpendicular to the direction of movement of valve member 194. As shown in FIG. 17, outlet passage 190 has a configuration that allows the portion of slot 204 that communicates therewith to increase as valve member 194 moves in an upward direction and to decrease as valve member 194 moves in a downward direction. When the slot moves above or below the outlet passage 190, the outlet passage is effectively closed. Although a generally triangularly shaped outlet passage and an elongated slot are shown to provide progressive discharge flow rate as described above, it should be understood that other configurations or mechanisms can be used.

In operation, when sufficient cerebrospinal fluid pressure exists, valve member 194 moves downwardly so that slot 204 is aligned with outlet passage 190 as shown in FIGS. 16 and 17. This allows the fluid to flow through the valve at the valve's maximum capacity and be discharged into a space within the patient's body such as the peritoneal cavity shown in FIG. 11. As the cerebrospinal fluid pressure increases, such as when the patient moves from a prone position toward a standing position, the valve member 194 moves downwardly decreasing the size of the opening between chamber 192 and outlet passage 190. A substantially constant flow rate is preferred and may be attained by selecting a spring rate and slit and outlet profiles which allow outlet resistance to change linearly with increasing pressure. The second valve 180 in the illustrative embodiment is selected to have a coil spring having a spring rate greater than the coil in valve 178 so that when the pressure of the fluid chamber 192 (which corresponds to the pressure in the ventricle, for example, plus the fluid height) increases to another value, such as when the patient assumes a standing upright position, its longitudinal slot aligns with its outlet passage so that fluid may flow through valve 180. At the same time, the increased pressure causes the valve member in valve 178 to move downwardly to the extent that slot 204 is no longer registered with outlet passage 188. At this time, the fluid only flows through valve 180 and not valve 178. In this manner, cerebrospinal removal apparatus 170 accommodates different pressure heads as the patient moves around.

In sum, the coil valve 178 is selected so that slot 204 is fully registered with outlet passage 190 when the patient is in a prone position and the patient's cerebrospinal fluid pressure is above the threshold value discussed above. As the patient approaches an upright position, valve member 194 moves downwardly to the extent it is no longer in register with outlet passage 190. Valve 180 includes the time a coil selected to allow its valve member, corresponding to valve member 194, to assume the position shown in FIG. 16 at the moment valve 178 closes due to the increased pressure. When the pressure continues to increase, valve 180 will progressively close in a manner similar to valve 178, but will not close in response to high pressure. It will, however, only allow the piston to travel to a point of maximum resistance. In this manner, the valve provides pressure relief.

The valve housing may comprise polycarbonate material and the valve member and piston may comprise polycarbonate or polytetrafluoroethylene. In addition, the valve member and piston may be integrally formed as a single member. The O-ring may comprise silicone, for example, any of the valves or pumps described above in connection with any of the foregoing embodiments.

In general, the coil springs are selected so that the flow rate of cerebrospinal fluid through valve 178 or 180 does not exceed about 1.5 ml per minute. In addition, a check valve 140 as described with reference to FIG. 14, may be included in apparatus 170 to ensure that cerebrospinal fluid does not flow toward the valves 178 and 180 when the cerebrospinal fluid pressure is below 6 cm $H_2O$.

Figure 19:
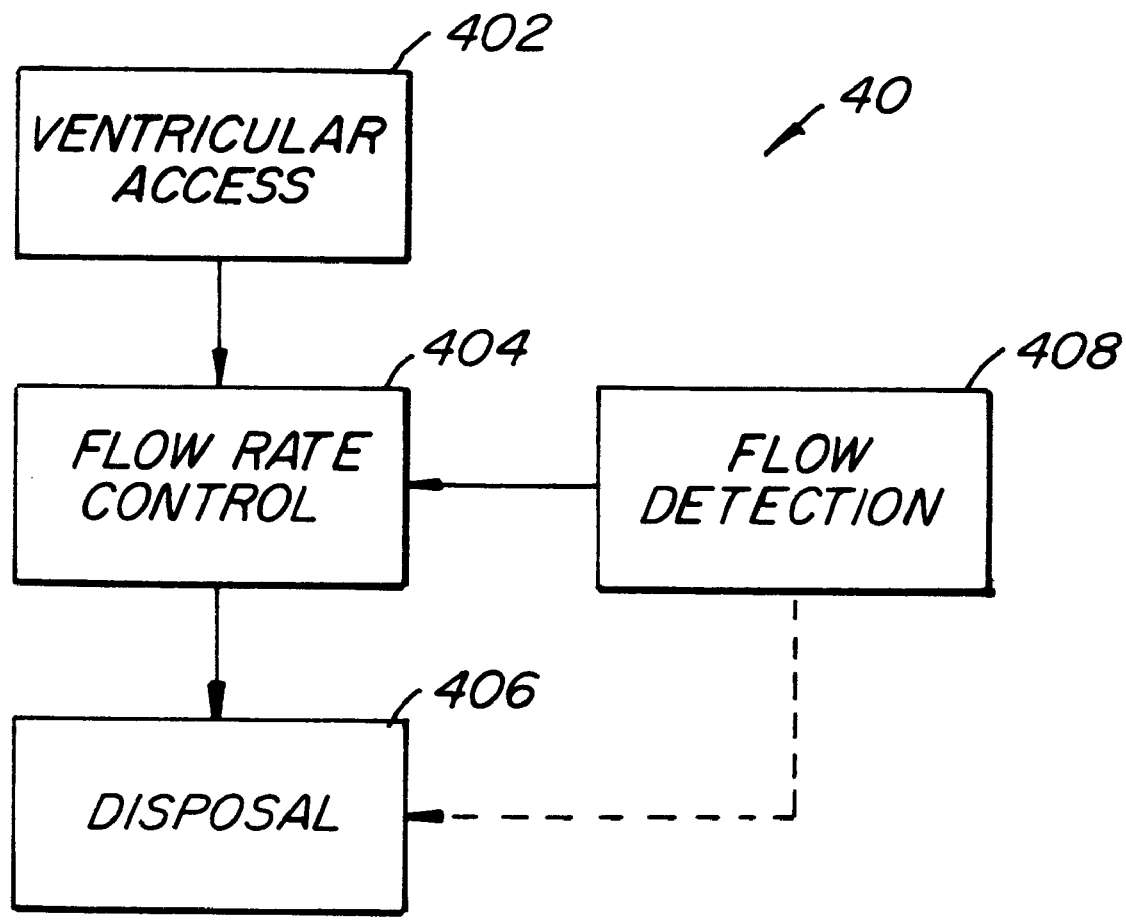
FIG. 19 is a schematic illustration of a catheter system which may be used to perform the methods of the present invention.

Methods of the present invention may be performed with catheter systems 400, as schematically shown in FIG. 19. Such systems will comprise a ventricular access component 402, a flow rate control component 404, a disposal component 406, and optionally a flow detection component 408. Many specific devices which can serve as one or more of such component(s) have already been described above. In general, the components may be provided integrally, e.g., as a single continuous catheter body having an access end, a disposal end, and flow rate control element(s) provided within the catheter body. Alternatively, any or each of the components may be provided as a discrete device or element and joined temporarily or removably to the other components of the system 400.

The ventricular access component 402 will usually comprise a catheter body having a plurality of inlet ports, generally as described above. The catheter body will have a distal end which is adapted for temporary or permanent (usually permanent) implantation in the subarachnoid space and will have a proximal end which either (1) forms the remainder of an integral catheter having all other system components incorporated therein or (2) is adapted for attachment to the flow rate control component 404. In the latter case, the ventricular access catheter body will usually terminate in an open lumen which can be attached to the flow rate control component 404 using a conventional port connector.

Figure 20A:
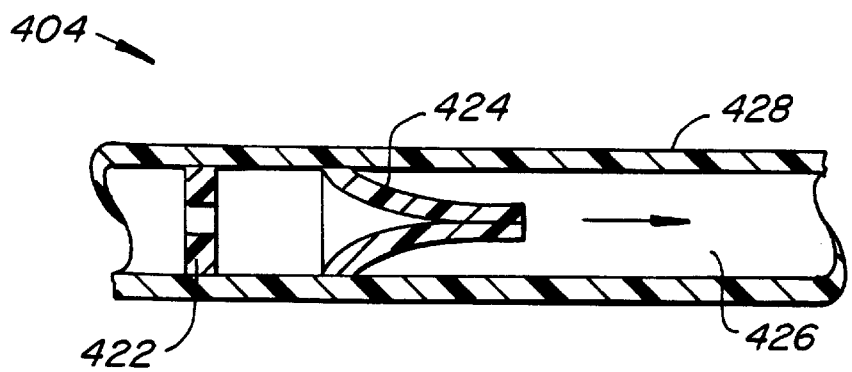
FIGS. 20A–20C illustrate alternative devices which may be used as the flow rate control component of the system of FIG. 19.
Figure 20B:
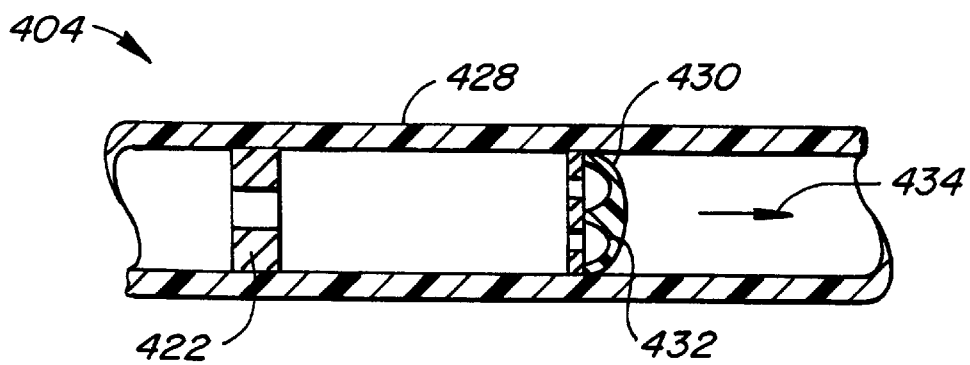
Figure 20C:
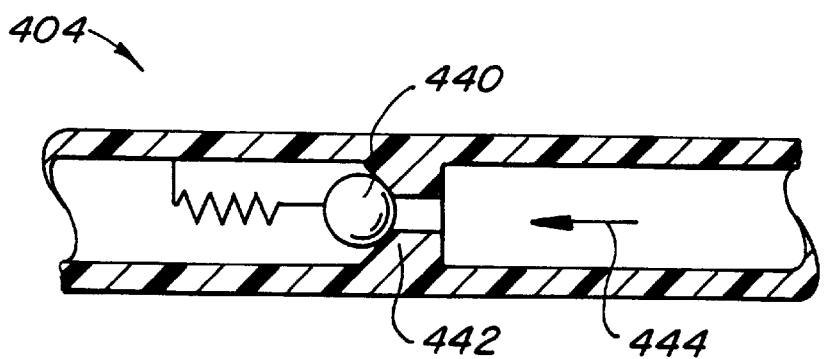

The flow rate control component 404 may comprise a discrete housing, typically having ports for connecting the ventricular access component 402 and the disposal component 406, or alternatively may be formed integrally within a catheter body. Particular flow rate control components are illustrated in FIGS. 20A, 20B, and 20C. In FIG. 20A, the flow rate control component 404 may comprise an orifice plate 422 in series with a one-way valve, illustrated as a duck-bill valve 424. Both the orifice plate 422 and duck-bill valve 424 may be mounted within lumen 426 of a catheter body 428, where catheter body 428 may be formed discretely or may be formed as part of either the ventricular access component 402 and/or the disposal component 406. Alternatively, the flow rate control component can comprise a variety of other flow restrictive elements, such as a multiple orifice plate, a filter element, or any other discrete element or combination of elements that can provide a flow resistance capable of yielding the flow rates described herein.

FIG. 20B illustrates a second exemplary flow rate control component 404 comprising an orifice plate 422 in series with an umbrella valve 430. The umbrella valve 430 includes an elastomeric membrane 432 which opens under pressure to permit flow in the direction of arrow 434. The catheter body 428 may also be included as a discrete component, or as part of the ventricular access component 402 or disposal component 406.

A third flow rate control component 404 is illustrated in FIG. 20C and comprises a spring-loaded ball valve 440 which is disposed in a valve seat 442. The valve seat 442 also serves as an orifice to limit flow through the assembly. Flow in direction of arrow 444 will open the ball valve 440 and permit flow through the orifice defined by valve seat 442.

In the above cases, the orifice can be selected to provide a desired flow rate when the patient is in a vertical position. The flow rate control component 404 will be implanted within the patient in known orientation, usually vertical, in order to provide a known pressure head of cerebrospinal fluid onto the orifice 422 or 442. The pressure will be sufficient to open the associated one-way valve (424, 430, or 440) and flow will be established when the patient is in an upright position. Suitable orifice diameters in the range from 0.03 mm to 0.4 mm, preferably from 0.1 mm to 0.2 mm, for orifices having a thickness in the range from 0.001 mm to 100 mm, preferably from 1 mm to 5 mm, in order to establish average hourly flow rates in the range from 0.5 ml/hour to 15 ml/hour, preferably 1 ml/hour to 3 ml/hour.

Figure 21A:
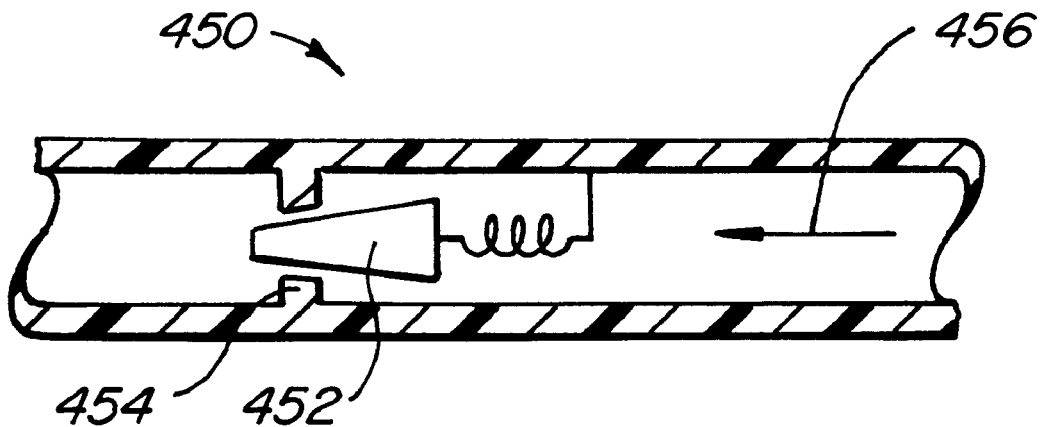
FIGS. 21A and 21B illustrate further alternative devices which may be used as the flow rate control component of the system of FIG. 19.
Figure 21B:
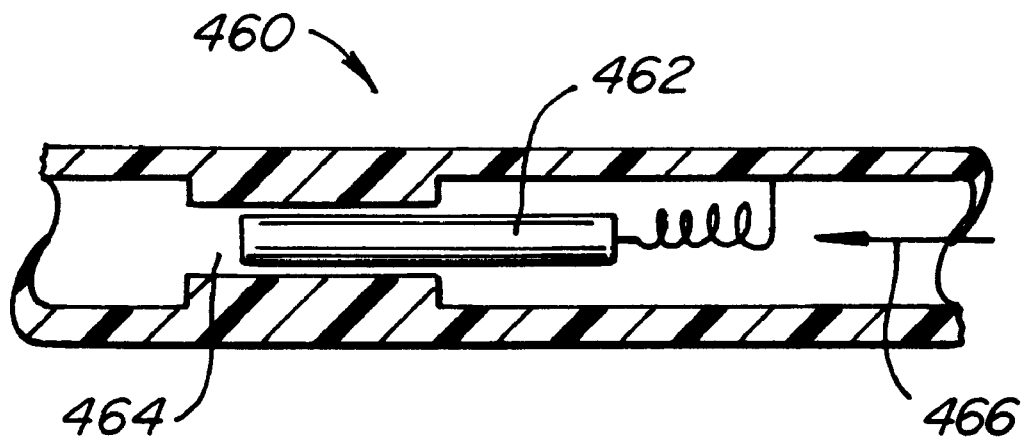

In order to avoid differences in flow rate resulting from differences in pressure, which may arise for example from changes in patient orientation or certain patient conditions, such as pericardial disease, hydrocephalus, etc., self-compensating valves may be provided as illustrated in FIGS. 21A and 21B. Valve 450 in FIG. 21A comprises a tapered plug 452 disposed to reciprocate axially relative to an aperture plate 454. The plug 452 is spring-loaded so that it closes upon flow in the direction of arrow 456. As the plug 454 closes, flow resistance is increased. Thus, higher pressures and higher flow rates automatically close the valve 450 to reduce the flow rate in a self-compensating manner.

Valve 460 in FIG. 21B operates similarly with an axially reciprocatable cylinder 462 being mounted in a tubular lumen 464. The cylinder 462 is spring-loaded so that flow in the direction of arrow 466 causes the cylinder to enter further into the lumen 464, thus increasing the flow resistance through the lumen 464. Such action also compensates any factors which would tend to increase flow through the lumen 464. Valve 460 does not inherently limit retrograde flow, so the system of FIG. 21B may further comprise a one-way valve.

Figure 22:
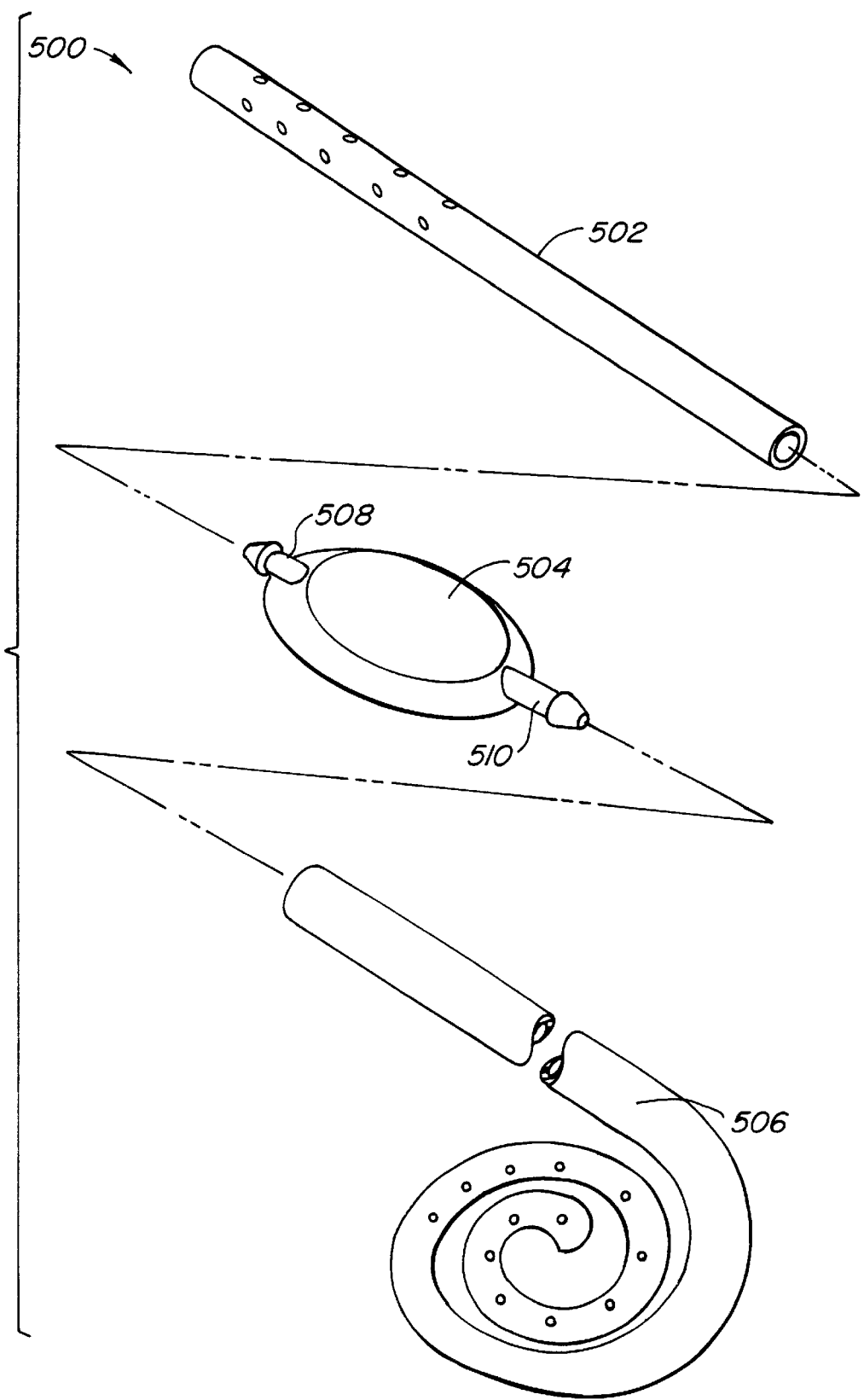
FIG. 22 illustrates a specific catheter system including a ventricular catheter, a flow rate control module, and a peritoneal catheter, constructed in accordance with the principles of the present invention.

An exemplary system 500 for performing the methods of the present invention is illustrated in FIG. 22. System 500 comprises a ventricular catheter 502, a flow rate control module 504, and a peritoneal disposal catheter 506. The ventricular catheter 502 typically has a length from 10 to 50 cm and a lumen diameter from 0.1 to 2 mm and is removably connectable to a port 508 on the flow rate control module 504. Similarly, the peritoneal disposal catheter 506 is removably connectable to a second port 510 on the flow rate control module 504. The system can be assembled prior to implantation. Conveniently, however, the various components of the system can be implanted separately, sized to the particular patient, and thereafter joined during the surgical implantation.

Figure 23:
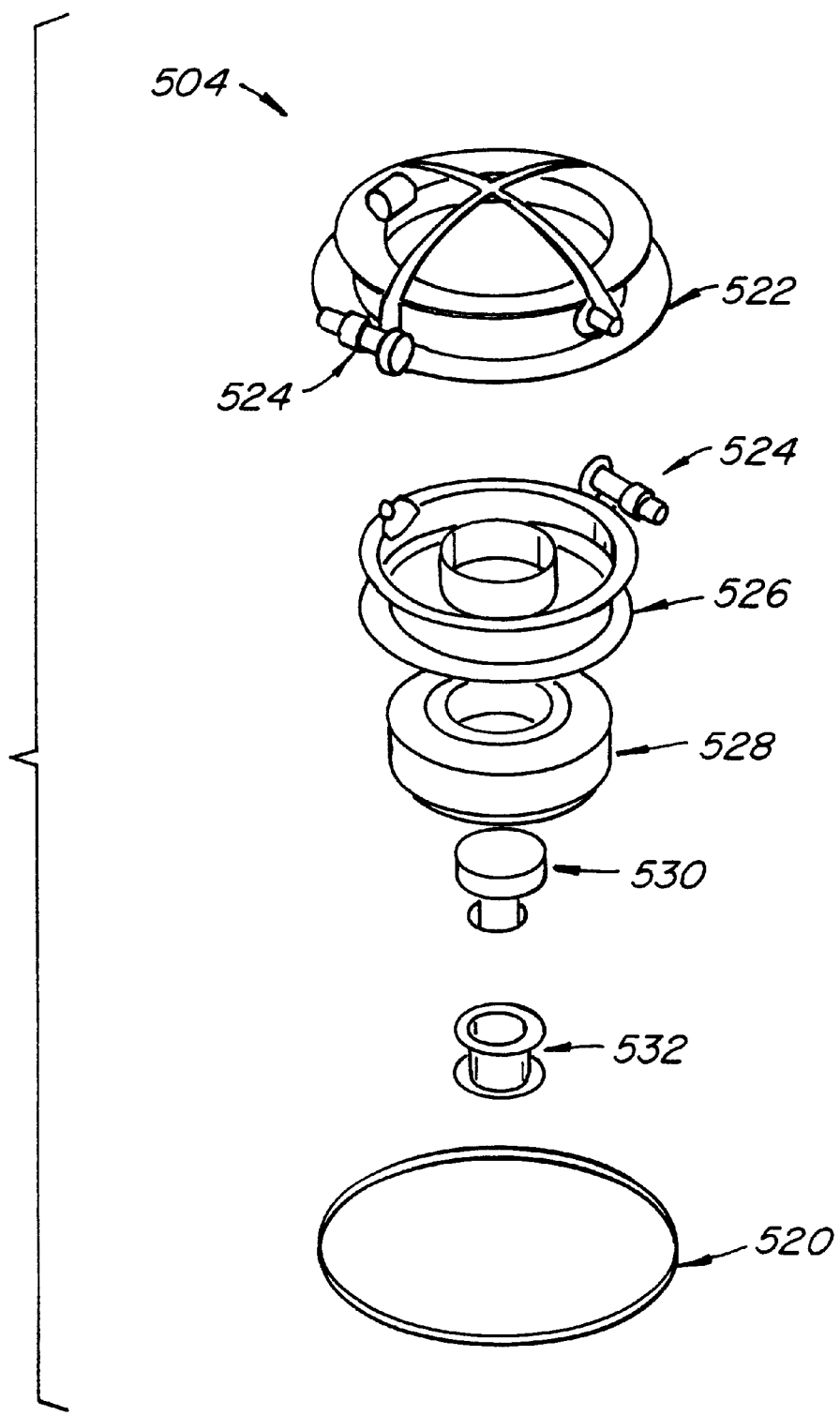
FIG. 23 illustrates the flow rate control module of FIG. 22, shown in an exploded view.
Figure 24:
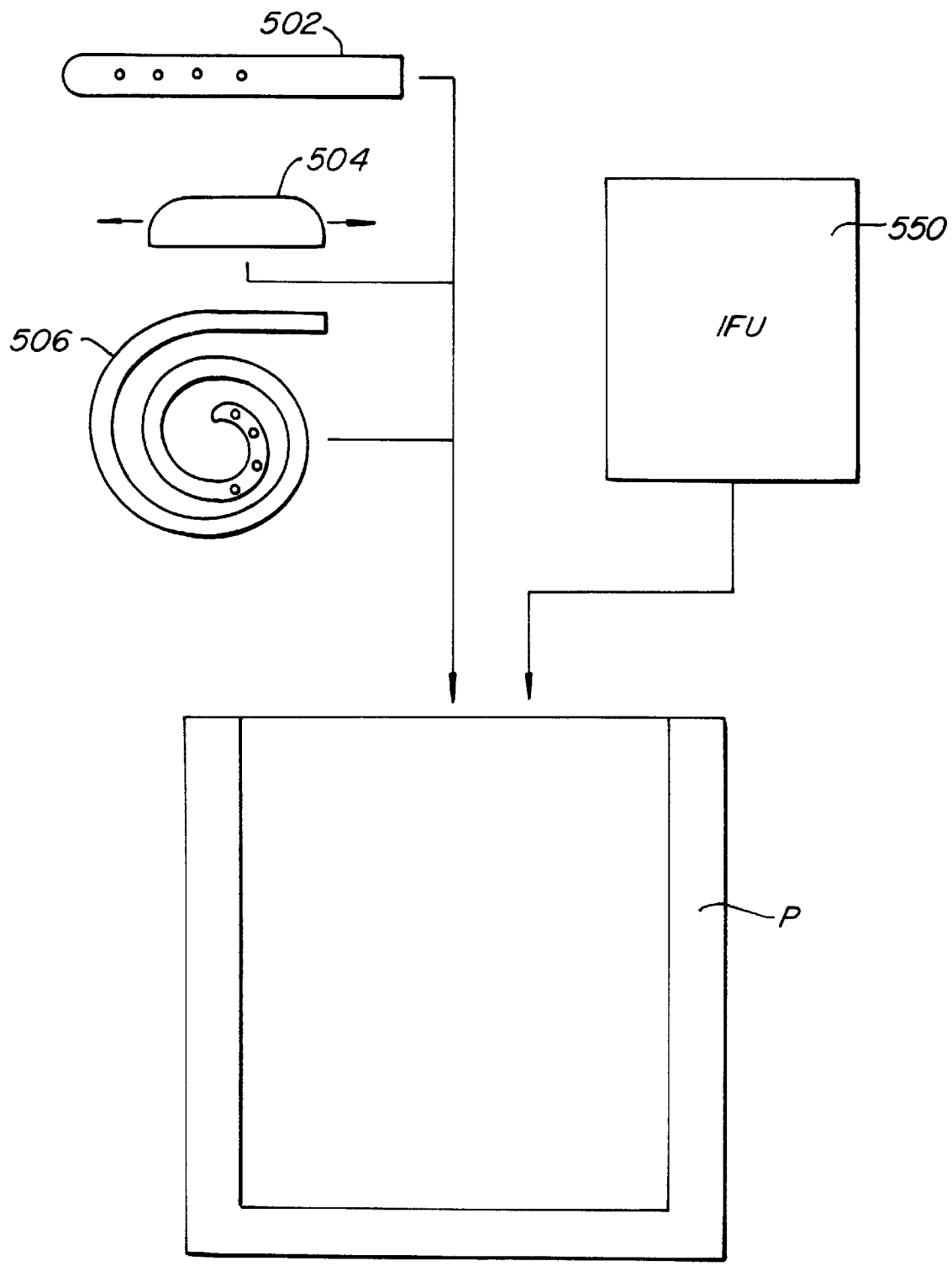
FIG. 24 illustrates a kit according to the present invention.

The flow rate control module 504 is illustrated in more detail in FIG. 23, and includes a base 520, a cap 522, barbs 524, and a flow resistor 526. The flow resistor 526 is a coiled tube, typically a silastic tube having a length in the range from 25 cm to 200 cm, usually being about 1 m in length with an inside diameter of in the range from 0.05 mm to 0.2 mm, usually being about 0.2 mm. The length, inside diameter, and other flow characteristics of the tube may be chosen to provide the desired flow resistance for the flow rate control module 504. The tubing of the flow resistor 526 will be held in a mandrel 528 and connected to a check valve 530 which is held in a ring 532. Thus, it can be seen that the valve control module 504 provides for both flow resistance and for unidirectional flow through the catheter system 500.

The peritoneal catheter 506 will typically have a length in the range from 25 cm to 125 cm and a lumen diameter in the range from 0.1 mm to 2 mm and may be formed similarly to peritoneal catheters used for peritoneal dialysis which are commercially available from a number of suppliers, such as Medtronic PS Medical, Baxter Healthcare, and Medos, S. A. In system 500, the flow resistances through both the ventricular catheter 502 and the peritoneal disposal catheter 506 will generally be much lower than the flow resistance afforded by the flow resistor 526 in the flow control module 504. In that way, the flow resistor 526 will control the flow rate through the catheter system 500. The flow control module 504 could also employ any of the other flow resistance components and elements described herein before, including active flow-compensating elements as illustrated in FIGS. 21A and 21B.

The flow detection component 408 illustrated in FIG. 19 may be provided in a variety of ways. Most simply, a flow responsive element, such as a valve component or other element which moves in response to flow therepast, may be provided in the flow control component 404 or elsewhere in the system. A sensitive motion detector, such as a fetal heart monitor, may then be used to detect motion which results from flow, thus confirming that flow is occurring. Usually, it will be desirable to enhance the detectability of the flow responsive element. For example, it may be possible to employ magnetic or magnetizable components as a portion of any of the one-way valve components illustrated in FIGS. 20A–20C. Alternatively, the spring-loaded ball valve 440 may be formed from a magnetic material and/or impregnated with a ferromagnetic material to enhance detectability using a SQUID.

In other cases, flow may be detected by releasing a detectable substance, such as a non-toxic fluorescent or other dye marker, into the cerebrospinal fluid as it passes through the flow rate control component 404 or elsewhere in the catheter system 400. A reservoir of such detectable substance may be provided in the flow rate control module 404 and connected to a lumen or catheter which release small amounts of the detectable substance into the cerebrospinal fluid through the flow control module or associated catheter. The substance may then be detectable in a patient sample, such as blood, urine, saliva, or other easily accessible patient specimen which can then be assayed for presence of the substance. In any case, if it is determined that flow has ceased or become undetectable, it will be necessary to access the catheter system and correct the problem and/or replace components of the system.

The systems of the present invention may be provided in a kit form, as illustrated in FIG. 23. The kit will include the system components, such as ventricular access catheter 502, flow control module 504, and peritoneal catheter 506, just described, together with instructions for use 550. The instructions for use 550 may set forth any of the methods described in the present application, including methods for implanting the system components within a patient so that the ventricular catheter is at the subarachnoid space, the flow control module is within the thoracic cavity, and the peritoneal catheter terminates within the peritoneum.

The system components and instructions for use will be provided within a package P, which may be in the form of a pouch, box, tray, tube, or other conventional medical package. The instructions for use 550 may be packaged within the package or may be printed on the package, or both. Usually, the system components will be sterilized within the package so they may be used without further sterilization.

The patient with Alzheimer's disease may be operated upon for implantation of the pressure driven pumps described above in the following manner: The patient will be completely anesthetized and incubated. The patient will be placed on the operating room table in the supine position. The scalp over the non-dominant parietal lobe will be shaved. An incision will be laid out over the parietal scalp, over the rib cage at about the mid-portion in the anterior axillary line, and in the abdomen. The three incision areas will be shaved, prepped, and draped in the usual fashion. The scalp incision will be open down to the bone and a burr hole placed. The urea will be coagulated, and a conduit will be placed into the lateral ventricle on that side. Another incision will be made over the rib cage at roughly the T5 or T6 level. The incision will be made parallel to the rib at its upper portion. The rib will then be dissected free of the underlying pleura and the pump will be positioned against the internal side of the rib and held in place with sutures into the rib periosteum. Using a shunt-passing cannula, tubing will then be led from the conduit in the ventricle under the skin down to the pump and connected there. Again, an incision is made in the abdomen overlying the rectus muscle on the same side and the incision carried down to the peritoneum will then be opened and a conduit will be dropped into the peritoneum and also led subcutaneously up to the pump. After all the connections are made, all the skin incisions are closed in the usual fashion. The patient will be treated with preoperative antibiotics and then will probably spend a day or two in the hospital before going home. Implantation of the other embodiments will be apparent to those of ordinary skill in the art in view of the foregoing description.

It is also noted that an indicator may be coupled to any one of the pumps described above to provide an audible signal in response to detecting that the pump is pumping fluid. A similar indicator may be coupled to any one of the valves described above to provide an audible indication of when fluid is flowing through a respective valve. Alternatively, the ball valve pump configurations may comprise material to facilitate monitoring the pump with a stethoscope.

Other modifications to the embodiments described above will be apparent to those skilled in the art. The disclosures of all prior art references described above are incorporated herein by reference.

What is claimed is:

1. An apparatus for removing cerebrospinal fluid comprising:

a conduit comprising a first opening and a second opening, the first opening of the conduit being adapted to be disposed in fluid communication with a space within a patient's subarachnoid space the second opening being adapted to be disposed in fluid communication with another portion of the patient's body; and a pump attached to the conduit between the first and second openings;

said pump being adapted for coupling to structure within the patient's body so that the pumping is effected by motion of the structure or changes in internal body pressure as the patient moves.

2. The apparatus of claim 1, wherein the pump has an outlet and the conduit is a first conduit, the second opening of the first conduit being in fluid communication with the pump outlet, the apparatus further comprising a second conduit having a first opening in fluid communication with the pump outlet and a second opening adapted for being placed in communication with space within the patient's subarachnoid space.

3. The apparatus of claim 2, wherein the device further comprises a valve for controlling flow from the pump outlet to the second conduit.

4. The apparatus of claim 1, wherein the pump comprises a bellows adapted for coupling to the structure within the patient's body.

5. The apparatus of claim 4, wherein the bellows is adapted to be powered by motion of the patient's diaphragm.

6. The apparatus of claim 1, wherein the pump is a piston pump and includes a piston slidably mounted therein.

7. The apparatus of claim 6, wherein the piston is adapted to be powered by changes in pressure in the patient's thoracic cavity.

8. The apparatus of claim 7, wherein the piston has a surface that is exposed to the environment external to the pump.

9. The apparatus of claim 1, wherein the pump is a diaphragm pump.

10. The apparatus of claim 9, wherein the pump has a diaphragm that forms an outer surface of the pump and is exposed to an internal body pressure environment external to the pump.

11. The apparatus of claim 9, wherein the diaphragm is adapted to be powered by pressure changes in the patient's thoracic cavity.

12. The apparatus of claim 1, further comprising a relief valve coupled to the conduit in the vicinity of the first opening.

* * * * *